United States Patent
Magistretti et al.

(10) Patent No.: US 11,925,632 B2
(45) Date of Patent: Mar. 12, 2024

(54) ISOQUINOLINE DERIVATIVES FOR USE IN TREATING GLUT1 DEFICIENCY SYNDROME

(71) Applicant: GLIAPHARM SA, Geneva (CH)

(72) Inventors: Pierre Magistretti, Crans-Montana (CH); Sylvain Lengacher, Lausanne (CH); Charles Finsterwald, Veyrier (CH); Timothy John Ritchie, St Albans (GB)

(73) Assignee: GLIAPHARM SA, Geneva (CH)

( * ) Notice: Subject to any disclaimer, the term of this patent is extended or adjusted under 35 U.S.C. 154(b) by 0 days.

(21) Appl. No.: 17/790,148

(22) PCT Filed: Dec. 29, 2020

(86) PCT No.: PCT/EP2020/087950
§ 371 (c)(1),
(2) Date: Jun. 30, 2022

(87) PCT Pub. No.: WO2021/136763
PCT Pub. Date: Jul. 8, 2021

(65) Prior Publication Data
US 2023/0102415 A1 Mar. 30, 2023

(30) Foreign Application Priority Data
Dec. 30, 2019 (EP) .................................... 19220107

(51) Int. Cl.
*A61K 31/47* (2006.01)
(52) U.S. Cl.
CPC .................................... *A61K 31/47* (2013.01)
(58) Field of Classification Search
CPC .............................. A61K 31/47; A61K 31/472
See application file for complete search history.

(56) References Cited

U.S. PATENT DOCUMENTS

| | | | |
|---|---|---|---|
| 2013/0096310 A1 | 4/2013 | Takayama et al. | |
| 2021/0275516 A1 | 9/2021 | Magistretti et al. | |

FOREIGN PATENT DOCUMENTS

| | | |
|---|---|---|
| CN | 106924258 | 7/2017 |
| JP | H08-238839 | 9/1996 |
| JP | 2012-072068 | 4/2012 |
| JP | 2016-504323 | 2/2016 |
| WO | WO 2011/162274 | 12/2011 |
| WO | WO 2014/093901 | 6/2014 |
| WO | WO 2020/007807 | 1/2020 |

OTHER PUBLICATIONS

Wan et al.; "C1-Benzyl and benzoyl isoquinoline synthesis through direct oxidative cross-dehydrogenative coupling with methyl arenes"; 2015; Chem. Commun.; 51: 13953-13956; DOI: 10.1039/c5cc04791a (Year: 2015).*

De Vivo, D. C. et al. "Defective Glucose Transport Across the Blood-Brain Barrier as a Cause of Persistent Hypoglycorrhachia, Seizures, and Developmental Delay" *The New England Journal of Medicine*, Sep. 5, 1991, pp. 703-709, vol. 325, No. 10.

Finsterwald, C. et al. "Astrocytes: New Targets for the Treatment of Neurodegenerative Diseases" *Current Pharmaceutical Design*, 2015, pp. 3570-3581, vol. 21, No. 25.

Gras, D. et al. "GLUT1 deficiency syndrome: An update" *Revue Neurologique*, 2014 (available online Nov. 20, 2013), pp. 91-99, vol. 170.

James, D. E. "The Mammalian Facilitative Glucose Transporter Family" *NIPS*, Apr. 1995, pp. 67-71, vol. 10.

Klepper, J. et al. "Effects of anticonvulsants on GLUT1-mediated glucose transport in GLUT1 deficiency syndrome in vitro" *Eur J. Pediatr*, 2003 (published online Dec. 6, 2002), pp. 84-89, vol. 162, No. 2.

Lee, Y. et al. "Oligodendroglia metabolically support axons and contribute to neurogeneration" *Nature*, Jul. 26, 2012, pp. 443-448, supplemental pp. 1-2, vol. 487.

Ludbrook, J. "Multiple Comparison Procedures Updated" *Clinical and Experimental Pharmacology and Physiology*, 1988, pp. 1032-1037, vol. 25, No. 12.

Maher, F. et al. "Glucose transporter proteins in brain" *The FASEB Journal*, Oct. 1994, pp. 1003-1011, vol. 8.

Mueckler, M. "Facilitative glucose transporter" *Eur. J. Biochem.*, 1994, pp. 713-725, vol. 219.

Mullen, S. A. et al. "Absence epilepsies with widely variable onset are a key feature of familial GLUT1 deficiency" *Neurology*, 2010, pp. 432-440, vol. 75.

Saari, R. et al. "Microwave-assisted synthesis of quinoline, isoquinoline, quinoxaline and quinazoline derivatives as CB2 receptor agonists" *Bioorganic & Medicinal Chemistry*, 2011 (available online Dec. 9, 2010), pp. 939-950, vol. 19, No. 2.

Seidner, G. et al. "GLUT-1 deficiency syndrome caused by haploinsufficiency of the blood-brain barrier hexose carrier" *Nature Genetics*, Feb. 1998, pp. 188-191, vol. 18.

Suzuki, A. et al. "Astrocyte-Neuron Lactate Transport Is Required for Long-Term Memory Formation" *Cell*, Mar. 4, 2011, pp. 810-823, vol. 144.

Tadi, M. et al. "Learning-Induced Gene Expression in the Hippocampus Reveals a Role of Neuron-Astrocyte Metabolic Coupling in Long Term Memory" *PLoS ONE*, Oct. 29, 2015, pp. 1-21.

Vigevano, F. et al. "Therapeutic approach to epileptic encephalopathies" *Epilepsia*, 2013, pp. 45-50, vol. 54 (Suppl. 8).

Wang, D. et al. "A mouse model for Glut-1 haploinsufficiency" *Human Molecular Genetics*, 2006, pp. 1169-1179, vol. 15, No. 7.

Yang, J. et al. "Lactate promotes plasticity gene expression by potentiating NMDA signaling in neurons" *PNAS*, Aug. 19, 2014, pp. 12228-12233, vol. 111, No. 33.

Written Opinion in International Application No. PCT/EP2020/087950, dated May 12, 2021, pp. 1-11.

\* cited by examiner

*Primary Examiner* — Timothy P Thomas
(74) *Attorney, Agent, or Firm* — SALIWANCHIK, LLOYD & EISENSCHENK

(57) ABSTRACT

The present invention relates to new agents useful for the prevention and/or treatment of GLUT1-DS and related methods using the same.

24 Claims, 6 Drawing Sheets
Specification includes a Sequence Listing.

ISOQUINOLINE DERIVATIVES FOR USE IN TREATING GLUT1 DEFICIENCY SYNDROME

CROSS-REFERENCE TO RELATED APPLICATION

This application is the U.S. national stage application of International Patent Application No. PCT/EP2020/087950, filed Dec. 29, 2020.

REFERENCE TO SEQUENCE LISTING

The Sequence Listing for this application is labeled "Seq-List.txt" which was created on May 31, 2022 and is 1 KB. The entire content of the sequence listing is incorporated herein by reference in its entirety.

FIELD OF THE INVENTION

The present invention relates generally to the field of lactate enhancing agents and in particular the use of lactate enhancing agents for the treatment of Glucose transporter 1 (or GLUT1) deficiency related disorders.

BACKGROUND OF THE INVENTION

The high metabolic requirements of the mammalian central nervous system require dedicated transporters for the facilitated transport of nutrients across the blood-brain barrier. Facilitated glucose transport in vertebrates is catalyzed by a family of transporters consisting of at least five functional isoforms with distinct tissue distributions, subcellular localizations and transport kinetics (Mueckler, 1994, *Eur. J. Biochem.* 219, 71-725; James, 1995, *News Physiol. Sci.* 10, 67-71). Several of these transporters are expressed in the mammalian brain (Maheret al. 1985, *FASEB, J.* 8, 1003-1011). Glucose transporter 1 (or GLUT1), also known as solute carrier family 2, facilitated glucose transporter member 1 (SLC2A1), is a protein that in humans is encoded by the SLC2A1 gene mapped to the short arm of chromosome 1.

Genetic disease caused by dysfunctional brain glucose transport due to mutations in SLC2A1 gene has been reported (Seidner, 1998, *Nat Genet,* 18:188-191). GLUT1 deficiency disorder or Glut 1 deficiency syndrome, also known as Glut1-DS or De Vivo disease, is a rare genetic metabolic disorder associated with a deficiency of GLUT1, the protein that transports glucose across the blood brain barrier and from the interstitial medium into astrocytes. GLUT1 has two significant types in the brain: 45k and 55k. GLUT1 45k is present on astrocyte and GLUT1 55k is present on capillaries in the brain. Both types are responsible for glucose transport and their deficiencies cause a low level of glucose in the cerebrospinal fluid (CSF).

GLUT1-DS has a prevalence estimated to be 1 in 90,000 people. Patients carrying hemizygosity of GLUT1 and nonsense mutations resulting in truncation of the GLUT-1 protein have normal circulating blood glucose, but low CSF lactate, persistent hypoglycorrachia (low CSF glucose) and diminished transport of hexose into isolated red blood cells (De ViVo et al., 1991, *N. Engl. J. Med.,* 325, 703-709).

SLC2A1 gene mutations have been also associated with a variety of neurologic disorders ranging from the classic GLUT1-DS with microcephaly, mental retardation, drug-resistant epilepsy, ataxia, and spasticity (De ViVo et al., 1991, supra; Seidner, 1998, supra) to less severe disorders including paroxysmal exercised-induced dyskinesia (PED) and idiopathic generalized epilepsies (IGE), either alone or in combination (Mullen et al, 2010, *Neurology,* 75: 432-440).

Symptoms of GLUT1-DS can vary in severity depending on the mutation in SLC2A1 gene. They include, without limitation, mental retardation, cognitive impairment, epilepsy and motor function problems (including ataxia, gait disturbance, dystonia, dysarthria, aberrant gaze saccades, spasticity, and other paroxysmal neurologic phenomena) (Gras et al, 2014, *Revue Neurologoqique* 170:91-99).

Glut1 deficiency is diagnosed with a cerebral spinal fluid (CSF) measurement of glucose compared with glucose concentration in plasma. A low CSF glucose concentration in the absence of low glucose blood concentration is indicative of GLUT1-DS. A diagnosis of GLUT1-DS includes the confirmation of deficient erythrocyte glucose uptake in the erythrocyte 3-O-methyl-D-glucose (OMG) assay and/or the confirmation by genetic testing that identifies the characteristic SLC2A1 gene mutation associated with the disorder.

There is, to date, no cure for GLUT1-DS. The only treatment approved for GLUT1-DS is the ketogenic diet, which may prevent seizure activity in many individuals with GLUT1-DS. The ketogenic diet is a high-fat, low-carbohydrate diet that causes the body to burn fat for energy instead of glucose. Although the ketogenic diet is effective in treating seizures, it is less effective in treating cognitive impairment or behavioral issues. The ketogenic diet is also effective in reducing the severity of movement disorders associated with the classical form of GLUT1-DS in approximately half of cases. It is even more effective in treating movement disorders in individuals with non-classical forms of Glut1 deficiency syndrome. Ketogenic diet leads to synthesis of ketone bodies (acetoacetate and beta-hydroxybutyrate) in the liver. These ketone bodies can enter the brain via GLUT1-independent mechanisms (via monocarboxylate transporters and diffusion). When they enter in neurons, they are converted in acetyl-CoA and enter the tricyclic acid (TCA) cycle as energy substrate in place of glucose-mediated energy source. Although ketogenic diet shows beneficial effects in symptomatic treatment in GLUT1-DS, it has limited clinical potential as the compliance rate is very low.

Given the absence of cure for GLUT1-DS, there is an urgent need to develop drugs for addressing this medical need.

SUMMARY OF THE INVENTION

The present invention is based on the unexpected findings of new molecules stimulating release of lactate, glucose uptake and glycogenolysis in primary astrocytes cell cultures in vitro and in mice in vivo and having neuroprotective effects in a mouse model of ALS and mnemonic effect in a mouse model of memory. Therefore, it is believed that lactate synthesis in the brain triggered by preparation of a compound according to the invention, can locally provide energy to neurons and stimulate glucose uptake and therefore be beneficial to patients suffering from GLUT1-DS.

A first aspect of the invention provides a compound of the invention, as well as tautomers, geometrical isomers, optically active forms, enantiomeric mixtures thereof, pharmaceutically acceptable salts, pharmaceutically active derivative and mixtures thereof for use in the prevention and/or treatment of a disorder or a disease associated with GLUT1-DS.

According to another, the invention provides a use of a compound of the invention as well as tautomers, geometrical isomers, optically active forms, enantiomeric mixtures thereof, pharmaceutically acceptable salts, pharmaceutically active derivative and mixtures thereof for the preparation of a pharmaceutical composition for the prevention and/or treatment of a disorder or a disease associated with GLUT1-DS.

According to another, the invention provides a method of preventing or treating a disorder or a disease associated with GLUT1-DS in a subject, said method comprising administering in a subject in need thereof a therapeutically effective amount of a compound of the invention, a tautomer, a geometrical isomer, an optically active form, an enantiomeric mixture, a pharmaceutically acceptable salt, a pharmaceutically active derivative thereof or a mixture thereof.

According to another, the invention provides methods of preparation of compounds according to the invention and intermediates thereof.

DETAILED DESCRIPTION

Figure 1:
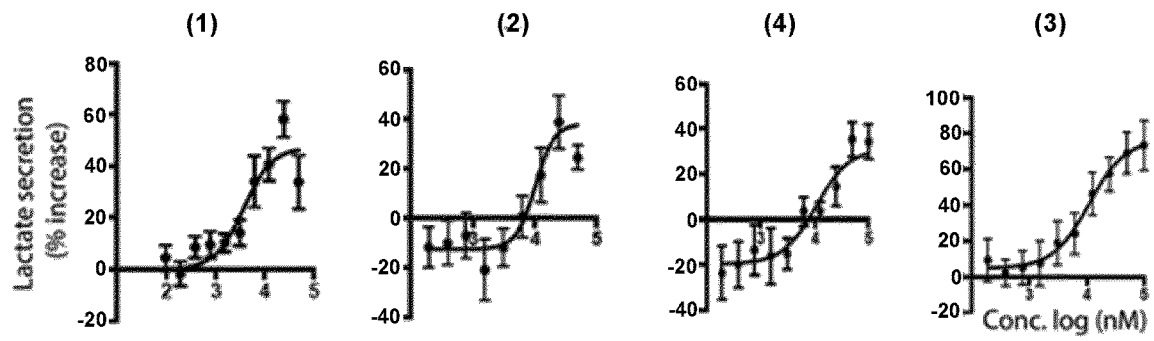
FIG. 1 shows the lactate release from primary cultures of astrocytes measured at 90 min after stimulation with compounds of the invention (1) to (4) at concentrations ranging from 100 nM to 100 µM as described in Example 2, represented as % of positive control effect (carbonyl cyanide m-chlorophenyl hydrazone (CCCP), 2 µM)±SEM; n=9.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful for enhancing lactate, particular in the treatment of GLUT1-DS.

The term "subject" as used herein refers to mammals. For examples, mammals contemplated by the present invention include human, primates, domesticated animals such as cattle, sheep, pigs, horses, laboratory rodents, other pets and the like.

The term "GLUT1-DS" according to the invention includes GLUT1 deficiency syndrome, Glucose transporter 1 deficiency syndrome, GLUT1 1 deficiency disorder, also known as De Vivo syndrome, De Vivo disease or De Vivo syndrome disease.

The term "effective amount" as used herein refers to an amount of at least one compound of the invention or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of compound of the invention sufficient to reduce the progression of the disease, notably to reduce or inhibit the progression of GLUT1-DS and thereby elicit the response being sought (i.e. an "effective amount").

The term "efficacy" of a treatment according to the invention can be measured based on changes in the course of disease in response to a use or a method according to the invention. For example, the efficacy of a treatment can be measured by an increase of glucose levels in the central nervous system and, or lactate levels in the central nervous system, as well as by imaging techniques including Positron Emission Tomography (PET) with fluorine-18 ($^{18}$F)-labeled 2-fluoro-2-deoxy-D-glucose as tracer or carbon-11, ($^{11}$C) Pittsburgh compound B (PIB), carbon-13 ($^{13}$C), phosphorus-31 ($^{31}$P), proton magnetic resonance spectroscopy ($^{1}$H) MRS to evaluate the bioenergetics status in the brain.

Effective treatment is indicated by an increase in cognitive performance (e.g. memory, reasoning test), reduction of epileptic seizures, their amplitude or frequency and treatment of motor function and movement disorders.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

Unless otherwise constrained by the definition of the individual substituent, the term "substituted" refers to groups substituted with from 1 to 5 substituents selected from the group consisting of "$C_1$-$C_6$ alkyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "cycloalkyl $C_1$-$C_6$ alkyl," "heterocycloalkyl $C_1$-$C_6$ alkyl," "amino," "aminosulfonyl," "ammonium," "alkoxy," "acyl amino," "amino carbonyl," "aryl," "aryl $C_1$-$C_6$ alkyl," "heteroaryl," "heteroaryl $C_1$-$C_6$ alkyl," "sulfinyl," "sulfonyl," "sulphonamide", "alkoxy," "alkoxy carbonyl," "carbamate," "sulfanyl," "halogen," "carboxy," trihalomethyl, cyano, hydroxy, mercapto, nitro, trihalo methyloxy, trihalo methylthio and the like.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting lactate enhancing activity that has a chemically or metabolically decomposable group, and a compound that may be converted into a pharmaceutically active compound in vivo under physiological conditions.

The prodrug is converted into a compound according to the present invention by a reaction with an enzyme, gastric acid or the like under a physiological condition in the living body, e.g. by oxidation, reduction, hydrolysis or the like, each of which is carried out enzymatically.

These compounds can be produced from compounds of the present invention according to well-known methods. The term "indirectly" also encompasses metabolites of compounds according to the invention.

The term "metabolite" refers to all molecules derived from any of the compounds according to the present invention in a cell or organism, preferably mammal.

In the context of the present invention are encompassed pharmaceutically acceptable salts, complexes, hydrates, solvates, or polymorphs, tautomers, geometrical isomers, optically active forms and pharmaceutically active derivatives of compounds of the invention. Unless stated to the contrary, the present invention includes all such possible diastereomers as well as their racemic mixtures, their substantially pure resolved enantiomers, all possible geometric isomers, and pharmaceutically acceptable salts thereof Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Many organic compounds exist in optically active forms having the ability to rotate the plane of plane-polarized light. In describing an optically active compound, the prefixes D and L or R and S are used to denote the absolute configuration of the molecule about its chiral center(s).

In the context of the present invention, «pharmaceutically acceptable salt thereof» refers to salts which are formed from acid addition salts formed with an acid, said acid may be an inorganic acid (e.g. hydrochloric acid, hydrobromic acid, sulfuric acid, phosphoric acid, nitric acid, and the like), or an organic acid such as acetic acid, fumaric acid, oxalic acid, tartaric acid, succinic acid, malic acid, malonic acid, fumaric acid, maleic acid, ascorbic acid, lactic acid or benzoic acid.

Pharmaceutically acceptable salts for the instant disclosure may be selected among salts formed with acids such as hydrochloric acid.

The term "pharmaceutical formulation" refers to preparations which are in such a form as to permit biological activity of the active ingredient(s) to be unequivocally effective and which contain no additional component which would be toxic to subjects to which the said formulation would be administered.

Compounds According to the Invention

According to a particular aspect of the invention, are provided compounds of Formula (I):

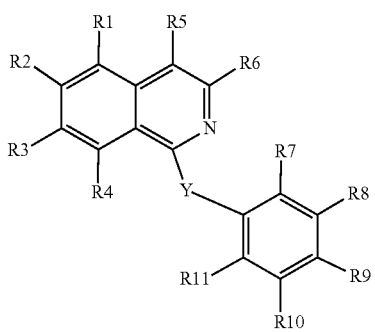

wherein $R^1$, $R^2$, $R^3$, $R^4$, $R^5$ and $R^6$ are independently selected from H, halogen (e.g. Cl or Br), optionally substituted alkoxy (e.g. optionally substituted methoxy), optionally substituted $C_1$-$C_6$ alkyl (e.g. optionally substituted methyl, optionally substituted ethyl), optionally substituted amine (e.g. dimethyl amine), optionally substituted carboxylic acid or ester (e.g. carboxylate), nitro and nitrile; $R^7$, $R^8$, $R^9$, $R^{10}$ and $R^{11}$ independently selected from H, halogen (e.g. Cl, F), optionally substituted alkoxy (e.g. optionally substituted methoxy, such as difluoromethoxy, trifluoromethoxy, 2-methoxyethoxy), optionally substituted $C_1$-$C_6$ alkyl (e.g. optionally substituted methyl such as trifluoromethyl, methyl, methoxy methyl), optionally substituted amine (e.g. dimethyl amine), optionally substituted carboxylic acid or ester, nitro and nitrile and a group of Formula (II): —$(X)_m$—$CR^{12}R^{13}R^{14}$ (II) wherein at least one group of $R^7$, $R^8$, $R^9$, $R^{10}$ and $R^{11}$ is a group of Formula (II); X is selected from O, $NR^{15}$, S, $SO_2$, $CH_2$ and hydrazine (—N—N—), m is an integer elected from 0 and 1 and $R^{12}$, $R^{13}$ and $R^{14}$ are independently selected from H, OH, optionally substituted alkoxy (e.g. optionally substituted methoxy), amide, pyrrolidone, nitrile, optionally substituted $C_1$-$C_6$ alkyl (e.g. optionally substituted methyl) and halogen (e.g. F); Y is selected from —$CR^{16}R^{17}$— and —$NR^{18}$—; $R^{15}$ is selected from H, optionally substituted alkoxy and optionally substituted $C_1$-$C_6$ alkyl; $R^{16}$ and $R^{17}$ are independently selected from H, halogen, optionally substituted alkoxy, optionally substituted $C_1$-$C_6$ alkyl and optionally substituted aryl; $R^{18}$ is independently selected from H or optionally substituted $C_1$-$C_6$ alkyl; any pharmaceutically acceptable salts, hydrates, solvates, or polymorphs, tautomers, geometrical isomers, optically active forms, enantiomeric mixtures thereof, and mixtures thereof, for the prevention, the repression or treatment of GLUT1-DS.

According to another particular aspect of the invention, are provided compounds for use according to the invention, wherein at least one of $R^{12}$, $R^{13}$ and $R^{14}$ is F or Cl.

According to another particular aspect of the invention, compounds of Formula (I) wherein X is selected from O, $NR^{15}$, S, $SO_2$ and hydrazine (—N—N—).

According to another particular aspect of the invention, $R^1$, $R^2$, $R^3$, $R^4$, $R^5$ and $R^6$ are independently selected from H, halogen, optionally substituted alkoxy such as methoxy, $C_1$-$C_6$ alkyl optionally substituted by halogen $C_1$-$C_6$ alkoxy, amino, nitro, optionally substituted amine, optionally substituted carboxylic acid or ester, nitro ($NO_2$) and nitrile.

According to another particular aspect of the invention, $R^1$ is H.

According to another particular aspect of the invention, $R^1$ is optionally substituted $C_1$-$C_6$ alkyl (e.g. optionally substituted methyl).

According to another particular aspect of the invention, $R^1$ is optionally substituted amine (e.g. dimethyl amine).

According to another particular aspect of the invention, $R^2$ is H.

According to another particular aspect of the invention, $R^2$ is optionally substituted $C_1$-$C_6$ alkyl (e.g. optionally substituted methyl or optionally substituted ethyl).

According to another particular aspect of the invention, $R^2$ is optionally substituted alkoxy (e.g. optionally substituted methoxy).

According to another particular aspect of the invention, $R^2$ is optionally substituted carboxylic acid or ester (e.g. carboxylate).

According to another particular aspect of the invention, $R^2$ is optionally substituted amine (e.g. dimethyl amine).

According to another particular aspect of the invention, $R^2$ is halogen or cyano.

According to another particular aspect of the invention, $R^3$ is H.

According to another particular aspect of the invention, $R^2$ is optionally substituted alkoxy (e.g. optionally substituted methoxy).

According to another particular aspect of the invention, $R^4$ is H.

According to another particular aspect of the invention, $R^5$ is H.

According to another particular aspect of the invention, $R^5$ is halogen.

According to another particular aspect of the invention, $R^5$ is optionally substituted $C_1$-$C_6$ alkyl (e.g. optionally substituted methyl).

According to another particular aspect of the invention, $R^6$ is H.

According to another particular aspect of the invention, $R^6$ is halogen.

According to another particular aspect of the invention, $R^7$ is H.

According to another particular aspect of the invention, $R^7$ is optionally substituted $C_1$-$C_6$ alkyl (e.g. optionally substituted methyl such as trifluoromethyl).

According to another particular aspect of the invention, $R^8$ is H.

According to another particular aspect of the invention, $R^8$ is halogen (e.g. Cl).

According to another particular aspect of the invention, $R^8$ is optionally substituted alkoxy (e.g. $OCF_3$ or $OCHF_2$).

According to another particular aspect of the invention, $R^8$ is optionally substituted amine (e.g. dimethyl amine).

According to another particular aspect of the invention, $R^9$ is H.

According to another particular aspect of the invention, $R^{10}$ is H.

According to another particular aspect of the invention, $R^{11}$ is H.

According to another particular aspect of the invention, $R^{10}$ and $R^{11}$ are H.

According to another particular aspect of the invention, $R^9$, $R^{10}$ and $R^{11}$ are H.

In a more particular embodiment, Y is —$NR^{18}$.

In another more particular embodiment, Y is —$CR^{16}R^{17}$.

In another more particular embodiment, Y is —$CR^{16}R^{17}$ and when one of $R^{16}$ and $R^{17}$ is a halogen, the other is not a halogen.

In a more particular embodiment $R^{18}$ is H.

In another more particular embodiment, $CR^{16}$ and $R^{17}$ are H.

In another more particular embodiment, $R^5$ and $R^6$ are H.

In another more particular embodiment, $R^1$ and $R^4$ are H.

In another more particular embodiment, $R^2$ and $R^3$ are independently selected from H and optionally substituted alkoxy such as methoxy.

In another more particular embodiment, $R^1$, $R^2$, $R^3$ and $R^4$ are H.

In another more particular embodiment, $R^1$ to $R^6$ are H.

In another more particular embodiment, $R^1$, $R^4$ and $R^6$ are H.

In another more particular embodiment $R^9$ is a group —$(X)_m$—$CR^{12}R^{13}R^{14}$.

In another more particular embodiment, $R^9$ is a group —$(X)_m$—$CR^{12}R^{13}R^{14}$ and $R^7$, $R^8$, $R^{10}$ and $R^{11}$ are H.

In another more particular embodiment, m is 1.

In another more particular embodiment, m is 0.

In another more particular embodiment, X is O.

In another more particular embodiment, X is S.

In another more particular embodiment, $R^{12}$, $R^{13}$ and $R^{14}$ are F.

In another more particular embodiment, $R^{12}$ and $R^{13}$ are H.

In another more particular embodiment, $R^{12}$ and $R^{13}$ are optionally substituted $C_1$-$C_6$ alkyl (e.g. optionally substituted methyl).

In another more particular embodiment, $R^{14}$ is optionally substituted $C_1$-$C_6$ alkoxy (e.g. methoxy).

In another more particular embodiment, $R^9$ is $OCF_3$.

In another more particular embodiment, $R^9$ is $CF_3$.

In another more particular embodiment, $R^9$ is CN.

In another more particular embodiment, $R^9$ is ($CH_2$) $OCH_3$.

In another more particular embodiment, a compound according to Formula (I) is not 1-[[4-(trifluoromethoxy) phenyl]methyl]isoquinoline.

In a more particular embodiment, compounds of the invention are selected from the following group:

6,7-dimethoxy-N-(4-(trifluoromethoxy)phenyl)isoquinolin-1-amine;
6,7-dimethoxy-N-(4-(trifluoromethyl)phenyl)isoquinolin-1-amine;
N-(4-(trifluoromethoxy)phenyl)isoquinolin-1-amine;
6,7-dimethoxy-1-(4-(trifluoromethoxy)benzyl)isoquinoline;
N-(3,4-dimethoxyphenyl)-6,7-dimethoxyisoquinolin-1-amine;
6,7-dimethoxy-N-(p-tolyl)isoquinolin-1-amine;
6,7-dimethoxy-N-(4-methoxyphenyl)isoquinolin-1-amine;
6,7-dimethoxy-N-(4-(2-methoxyethoxy)phenyl)isoquinolin-1-amine;
6,7-dimethoxy-N-(4-(methoxymethyl)phenyl)isoquinolin-1-amine;
N-(2-fluoro-4-(trifluoromethoxy)phenyl)-6,7-dimethoxyisoquinolin-1-amine;
6,7-dimethoxy-N-(3-(trifluoromethoxy)phenyl)isoquinolin-1-amine;
6-methoxy-N-(4-(trifluoromethoxy)phenyl)isoquinolin-1-amine;
6-chloro-N-(4-(trifluoromethoxy)phenyl)isoquinolin-1-amine;
N-(3-fluoro-4-(trifluoromethoxy)phenyl)-6,7-dimethoxyisoquinolin-1-amine;
$N^1$-(6,7-dimethoxyisoquinolin-1-yl)-$N^3$,$N^3$-dimethylbenzene-1,3-diamine;
N-(3-(difluoromethoxy)phenyl)-6,7-dimethoxyisoquinolin-1-amine;
4-((6,7-dimethoxyisoquinolin-1-yl)amino)-3-(trifluoromethyl)benzo-nitrile;
6,7-dimethoxy-N-(4-(methylthio)phenyl)isoquinolin-1-amine;
N-(3-chloro-4-(trifluoromethoxy)phenyl)-6,7-dimethoxyisoquinolin-1-amine;
6,7-dimethoxy-N-(4-(2-methoxyethyl)phenyl)isoquinolin-1-amine;
6-methoxy-5-methyl-N-(4-(trifluoromethoxy)phenyl)isoquinolin-1-amine;
6-methoxy-$N^5$,$N^5$-dimethyl-$N^1$-(4-(trifluoromethoxy)phenyl)isoquino-line-1,5-diamine;
4-chloro-6-methoxy-N-(4-(trifluoromethoxy)phenyl)isoquinolin-1-amine;
6-methoxy-4-methyl-N-(4-(trifluoromethoxy)phenyl)isoquinolin-1-amine;
4-bromo-6-methoxy-N-(4-(trifluoromethoxy)phenyl)isoquinolin-1-amine;
6-methoxy-4-methyl-N-(4-(trifluoromethoxy)phenyl)isoquinolin-1-amine;
$N^6$,$N^6$-dimethyl-$N^1$-(4-(trifluoromethoxy)phenyl)isoquinoline-1,6-diamine;
1-((4-(trifluoromethoxy)phenyl)amino)isoquinoline-6-carbonitrile;
methyl 1-((4-(trifluoromethoxy)phenyl)amino)isoquinoline-6-carboxylate; and
6-ethyl-N-(4-(trifluoromethoxy)phenyl)isoquinolin-1-amine; and any pharmaceutically acceptable salts, complexes, hydrates, solvates, or polymorphs, tautomers, geometrical isomers, optically active forms and pharmaceutically active.

According to a particular aspect of the invention, are provided compounds of the invention and their pharmaceutically acceptable salts selected among salts formed with hydrochloric acid or hydrobromic acid, sulfuric acid, phosphoric acid, nitric acid, and the like, or an organic acid such as acetic acid, fumaric acid, oxalic acid, tartaric acid, succinic acid, malic acid, malonic acid, fumaric acid, maleic acid, ascorbic acid, lactic acid or benzoic acid.

In a more particular embodiment, compounds of the invention are selected from the following group:

6,7-dimethoxy-N-(4-(trifluoromethoxy)phenyl)isoquinolin-1-amine;
6,7-dimethoxy-N-(4-(trifluoromethyl)phenyl)isoquinolin-1-amine;
N-(4-(trifluoromethoxy)phenyl)isoquinolin-1-amine hydrochloride; and
6,7-dimethoxy-1-(4-(trifluoromethoxy)benzyl)isoquinoline.

In another particular embodiment, compounds of the invention are selected from the following group:

N-(3,4-dimethoxyphenyl)-6,7-dimethoxyisoquinolin-1-amine;

6,7-dimethoxy-N-(p-tolyl)isoquinolin-1-amine;

6,7-dimethoxy-N-(4-methoxyphenyl)isoquinolin-1-amine;

6,7-dimethoxy-N-(4-(2-methoxyethoxy)phenyl)isoquinolin-1-amine;

6,7-dimethoxy-N-(4-(methoxymethyl)phenyl)isoquinolin-1-amine;

N-(2-fluoro-4-(trifluoromethoxy)phenyl)-6,7-dimethoxyisoquinolin-1-amine;

6,7-dimethoxy-N-(3-(trifluoromethoxy)phenyl)isoquinolin-1-amine;

6-methoxy-N-(4-(trifluoromethoxy)phenyl)isoquinolin-1-amine;

6-chloro-N-(4-(trifluoromethoxy)phenyl)isoquinolin-1-amine;

N-(3-fluoro-4-(trifluoromethoxy)phenyl)-6,7-dimethoxyisoquinolin-1-amine;

$N^1$-(6,7-dimethoxyisoquinolin-1-yl)-$N^3$,$N^3$-dimethylbenzene-1,3-diamine;

N-(3-(difluoromethoxy)phenyl)-6,7-dimethoxyisoquinolin-1-amine;

4-(((6,7-dimethoxyisoquinolin-1-yl)amino)-3-(trifluoromethyl)benzo-nitrile;

6,7-dimethoxy-N-(4-(methylthio)phenyl)isoquinolin-1-amine;

N-(3-chloro-4-(trifluoromethoxy)phenyl)-6,7-dimethoxyisoquinolin-1-amine;

6,7-dimethoxy-N-(4-(2-methoxyethyl)phenyl)isoquinolin-1-amine;

6-methoxy-5-methyl-N-(4-(trifluoromethoxy)phenyl)isoquinolin-1-amine;

6-methoxy-$N^5$,$N^5$-dimethyl-$N^1$-(4-(trifluoromethoxy)phenyl)isoquino-line-1,5-diamine;

4-chloro-6-methoxy-N-(4-(trifluoromethoxy)phenyl)isoquinolin-1-amine;

6-methoxy-4-methyl-N-(4-(trifluoromethoxy)phenyl)isoquinolin-1-amine;

4-bromo-6-methoxy-N-(4-(trifluoromethoxy)phenyl)isoquinolin-1-amine;

6-methoxy-4-methyl-N-(4-(trifluoromethoxy)phenyl)isoquinolin-1-amine;

$N^6$,$N^6$-dimethyl-$N^1$-(4-(trifluoromethoxy)phenyl)isoquinoline-1,6-diamine;

1-((4-(trifluoromethoxy)phenyl)amino)isoquinoline-6-carbonitrile;

methyl 1-((4-(trifluoromethoxy)phenyl)amino)isoquinoline-6-carboxylate;

N-(3,4-dimethoxyphenyl)-6,7-dimethoxyisoquinolin-1-amine;

6,7-dimethoxy-N-(p-tolyl)isoquinolin-1-amine;

6,7-dimethoxy-N-(4-methoxyphenyl)isoquinolin-1-amine;

6,7-dimethoxy-N-(4-(2-methoxyethoxy)phenyl)isoquinolin-1-amine;

6,7-dimethoxy-N-(4-(methoxymethyl)phenyl)isoquinolin-1-amine;

N-(2-fluoro-4-(trifluoromethoxy)phenyl)-6,7-dimethoxyisoquinolin-1-amine;

6,7-dimethoxy-N-(3-(trifluoromethoxy)phenyl)isoquinolin-1-amine;

6-methoxy-N-(4-(trifluoromethoxy)phenyl)isoquinolin-1-amine;

6-chloro-N-(4-(trifluoromethoxy)phenyl)isoquinolin-1-amine;

N-(3-fluoro-4-(trifluoromethoxy)phenyl)-6,7-dimethoxyisoquinolin-1-amine;

$N^1$-(6,7-dimethoxyisoquinolin-1-yl)-$N^3$,$N^3$-dimethylbenzene-1,3-diamine;

N-(3-(difluoromethoxy)phenyl)-6,7-dimethoxyisoquinolin-1-amine;

$N^1$-(6,7-dimethoxyisoquinolin-1-yl)amino)-3-(trifluoromethyl)benzo-nitrile;

6,7-dimethoxy-N-(4-(methylthio)phenyl)isoquinolin-1-amine;

N-(3-chloro-4-(trifluoromethoxy)phenyl)-6,7-dimethoxyisoquinolin-1-amine;

6,7-dimethoxy-N-(4-(2-methoxyethyl)phenyl)isoquinolin-1-amine;

6-methoxy-5-methyl-N-(4-(trifluoromethoxy)phenyl)isoquinolin-1-amine;

6-methoxy-$N^5$,$N^5$-dimethyl-$N^1$-(4-(trifluoromethoxy)phenyl)isoquino-line-1,5-diamine;

4-chloro-6-methoxy-N-(4-(trifluoromethoxy)phenyl)isoquinolin-1-amine;

6-methoxy-4-methyl-N-(4-(trifluoromethoxy)phenyl)isoquinolin-1-amine;

4-bromo-6-methoxy-N-(4-(trifluoromethoxy)phenyl)isoquinolin-1-amine;

6-methoxy-4-methyl-N-(4-(trifluoromethoxy)phenyl)isoquinolin-1-amine;

$N^6$,$N^6$-dimethyl-$N^1$-(4-(trifluoromethoxy)phenyl)isoquinoline-1,6-diamine;

1-((4-(trifluoromethoxy)phenyl)amino)isoquinoline-6-carbonitrile;

methyl 1-((4-(trifluoromethoxy)phenyl)amino)isoquinoline-6-carboxylate; and 6-ethyl-N-(4-(trifluoromethoxy)phenyl)isoquinolin-1-amine; and any pharmaceutically acceptable salts, complexes, hydrates, solvates, or polymorphs, tautomers, geometrical isomers, optically active forms and pharmaceutically active, pharmaceutical formulations thereof and those compounds for use as a medicament.

Among the salts of the compounds of the invention that can be made especially of the salts selected from the following list:

6,7-dimethoxy-N-(4-(trifluoromethoxy)phenyl)isoquinolin-1-amine hydrochloride;

6,7-dimethoxy-N-(4-(trifluoromethyl)phenyl)isoquinolin-1-amine hydrochloride;

N-(4-(trifluoromethoxy)phenyl)isoquinolin-1-amine hydrochloride; and 6,7-dimethoxy-1-(4-(trifluoromethoxy)benzyl)isoquinoline hydrochloride.

Pharmaceutical composition comprise at least one compound of Formula (I) as defined herein and a pharmaceutically acceptable carrier, diluent or excipient thereof wherein said at least one compound is not a compound selected from the following list:

N-[2-(trifluoromethyl)phenyl]isoquinolin-1-amine;

N-[3-(trifluoromethyl)phenyl]isoquinolin-1-amine; and

N-[4-(trifluoromethyl)phenyl]isoquinolin-1-amine.

The compounds of invention have been named according the IUPAC standards used in the ChemDraw (product version ultra 20.0).

According to another aspect the invention, a process for the preparation of a compound according to Formula (I) comprises the step of reacting an aniline intermediate of Formula (iii) with an intermediate of Formula (1) wherein Z is a leaving group selected from Iodine, Bromide Chloride, O-triflate or the like in a polar solvent to form a compound of Formula (Ia):

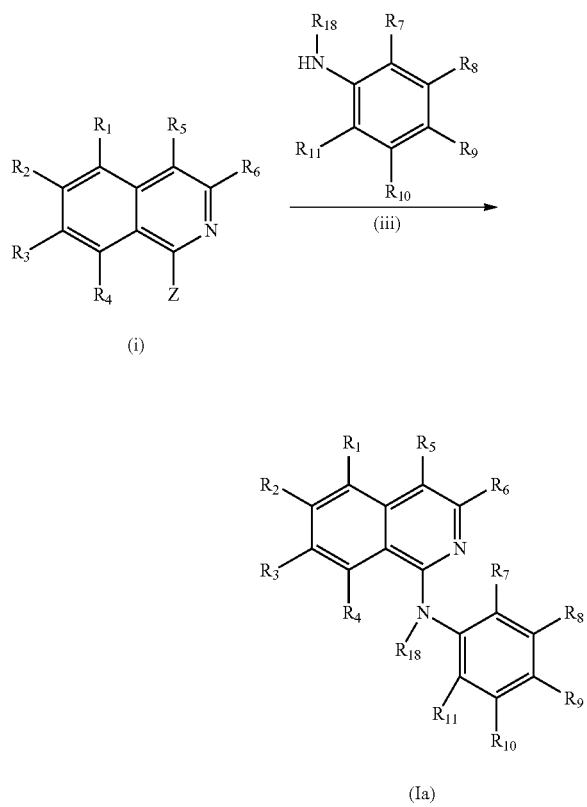

According to another aspect, a process for the preparation of a compound according to Formula (I), comprises the step of reacting a compound of Formula (Ia) wherein $R_{18}$ is H to lead to a compound of Formula (I) wherein $R^{18}$ is an optionally substituted $C_1$-$C_6$ alkyl (e.g. by N-alkylation).

According to another aspect, a process for the preparation of a compound according to Formula (I) comprises a reduction step of a carbonyl intermediate of Formula (viii) (e.g. by $NaBH_3CN$ in the presence of $ZnCl_2$ or by catalytic hydrogenation ($H_2$ in the presence of Pd/C and acid trace) to lead to a compound of Formula (Iab):

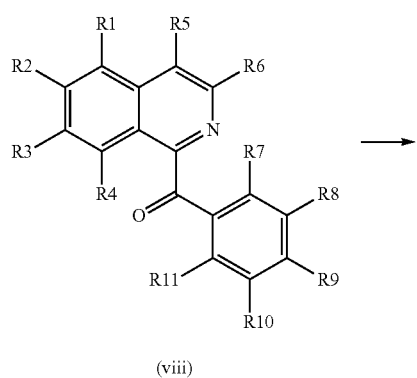

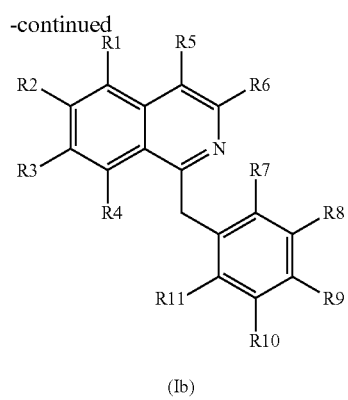

According to another aspect, a process for the preparation of a compound according to Formula (I) wherein the carbonyl group of an intermediate (viii) is reduced to lead to a compound of Formula (I) wherein at least one of the groups $R^{16}$ and $R^{17}$ is a halogen, an optionally substituted optionally substituted alkoxy, an optionally substituted $C_1$-$C_6$ alkyl, or an optionally substituted aryl (e.g. through a Grignard reaction or reacting an intermediate (viii) with (Diethylamino)sulfur trifluoride).

Compositions According to the Invention

The invention provides pharmaceutical or therapeutic agents as compositions and methods useful for treating a subject, preferably a mammalian subject, and most preferably a human patient who is suffering from GLUT1-DS.

Agent of the invention or formulations thereof may be administered as a pharmaceutical formulation, which can contain one or more agents according to the invention in any form described herein. The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of this invention may be liquid formulations including, but not limited to aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methylcellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions of this invention may also be formulated as a depot preparation, which may be administered by implantation or by intramuscular injection.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

The compounds of this invention can also be administered in sustained release forms or from sustained release drug delivery systems.

According to a particular embodiment, compositions according to the invention are for intravenous use.

According to a particular aspect, the formulations of the invention are oral formulations.

In another particular aspect, the compositions according to the invention are adapted for delivery by repeated administration.

According to a particular embodiment, compositions of the invention are veterinary compositions.

Further materials as well as formulation processing techniques and the like are set out in *Part 5 of Remington's "The Science and Practice of Pharmacy", 22$^{nd}$ Edition, 2012, University of the Sciences in Philadelphia, Lippincott Williams & Wilkins*, which is incorporated herein by reference.

Mode of Administration

Compounds and formulations thereof according to this invention may be administered in any manner including orally, parenterally, intravenously, intrathecally, rectally, or combinations thereof. Compounds and formulations thereof according to this invention may be also administered by inhalation or intradermally. Parenteral administration includes, but is not limited to, intravenous, intra-arterial, intra-peritoneal, subcutaneous and intramuscular. The compositions of this invention may also be administered in the form of an implant, which allows slow release of the compositions as well as a slow controlled i.v. infusion.

Combination

According to the invention, compounds and pharmaceutical formulations thereof can be administered alone or in combination with a co-agent or a co-treatment useful for treating, and/or stabilizing used for the treatment of GLUT1-DS or associated symptoms that include cognitive impairment, motor function and movement disorders or epileptic seizures. Such co-agents or co-treatments would include, but would not be limited to, at least co-agent useful for treating and/or stabilizing GLUT1-DS or associated symptoms including gene therapy for restoring GLUT1 expression, a ketogenic diet or a pharmaceutical compound regulating the synthesis of ketone bodies such as, for example, triheptanoin.

The invention encompasses the administration of a compound of the invention or a formulation thereof wherein it is administered to a subject prior to, simultaneously or sequentially with other therapeutic regimens or co-agents useful for treating, and/or stabilizing symptoms associated with GLUT1-DS, including, but not limited to, cognitive impairment, motor function and movement disorders or epileptic seizures.

A compound of the invention or a formulation thereof according to the invention that is administered simultaneously with said co-agents can be administered in the same or different composition(s) and by the same or different route(s) of administration.

According to one embodiment, is provided a pharmaceutical formulation comprising a compound of the invention combined with at least one co-agent useful for treating, and/or stabilizing, a neurodegenerative disorder and at least one pharmaceutically acceptable carrier.

The determination of the optimal combination and dosages can be determined and optimized using methods well known in the art.

The therapeutic agent according to the present invention and one or more other therapeutic agents can be administered in either order or simultaneously.

Methods According to the Invention

According to another aspect, the invention provides a method of preventing or treating a disorder related to GLUT1-DS.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

The invention having been described, the following examples are presented by way of illustration, and not limitation.

Synthesis of Compounds of the Invention

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approaches for obtaining compounds of Formula (I) are depicted in Schemes 1, 1-a, 1-b, 1-c, 1-d and 2 below.

Compounds of Formula (I), wherein Y is NH (Formula Ia) can be synthesized as described in Scheme 1 below. An isoquinoline intermediate of Formula (i) wherein Z can be Iodine, Bromide, Chlorine, or O-triflate is reacted with an acid HA such as trifluoroacetic acid or an alkyl sulfonic acid derivative (e.g. methyl sulfonic acid or trifluoromethylsulfonic acid) in a polar solvent such as isopropanol to form an activated salt form of the intermediate of Formula (ii).

Scheme 1

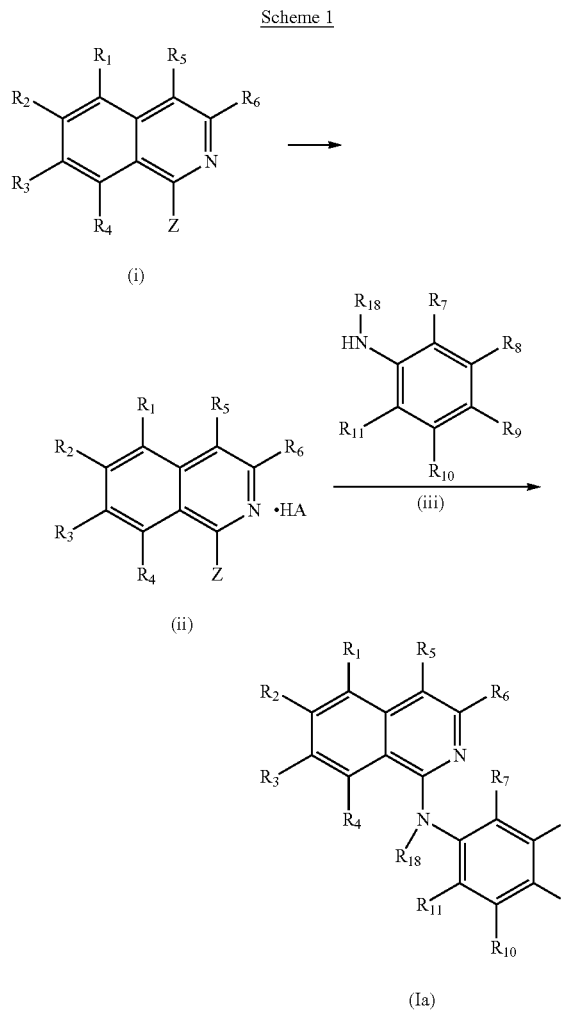

Then, an aniline intermediate of Formula (iii) is added to the intermediate of Formula (ii) in a polar solvent such as tert-butanol and the mixture is let reacted under reflux overnight and then after cooling, hydrolysed in presence of a base such as with a saturated $NaHCO_3$, $Na_2CO_3$, $KHCO_3$, $K_2CO_3$, NaOH or diluted KOH solution. After extraction, e.g. with dichloromethane drying and evaporation under reduced pressure, the crude is separated on silica gel to lead to a compound of Formula (Ia).

Alternatively, the aniline (iii) can be reacted with an intermediate (i) in similar conditions to directly obtain compounds of Formula (Ia).

Other compounds of Formula (I), wherein Y is NH (Formula (Ia)) can also be synthesized from compounds of Formula (Ia) wherein $R^1$ is a halogen X (Formula (ix)) as described in Scheme 1-a below.

Compounds of Formula (ix) wherein X can be Iodine, Bromide or Chlorine is reacted in a cross-coupling reaction with an organometallic reagent like for example a boronic acid or ester $R1B(OR)_2$ or an amine, in the presence of a catalyst/ligand system like for example $Pd(OAc)_2$/tricyclohexylphosphine or tBuXPhos Pd G3, a base like for example $K_2CO_3$ or t-BuONa, in a solvent like for example DMF or THF.

Scheme 1-a

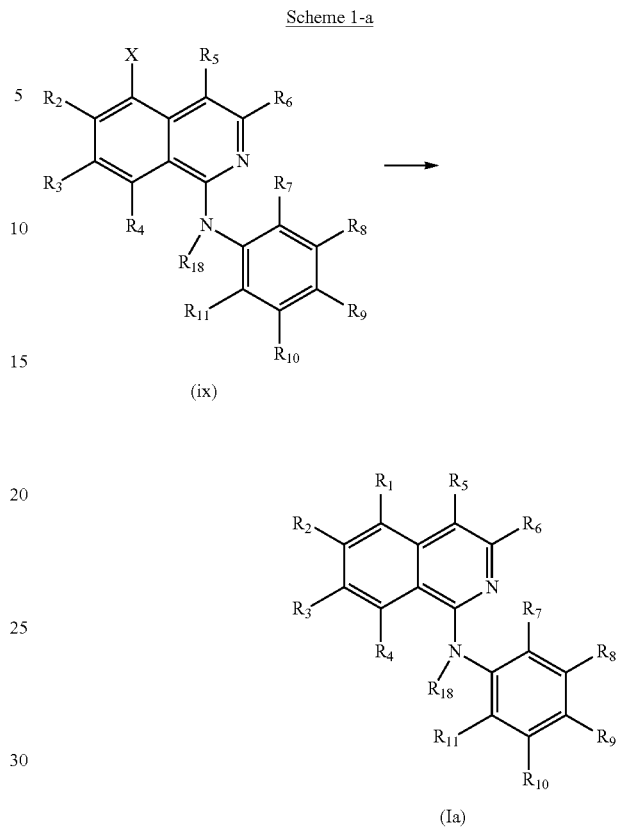

Other compounds of Formula (I), wherein Y is NH (Formula Ia) can also be synthesized from compounds of Formula (Ia) wherein $R^5$ is a halogen X (Formula (x)) as described in Scheme 1-b below.

Compounds of Formula (x) wherein X can be Iodine, Bromide or Chlorine is reacted in a cross-coupling reaction with an organometallic reagent like for example a boronic acid or ester $R1B(OR)_2$ or an amine, in the presence of a catalyst/ligand system like for example $Pd(OAc)_2$/tricyclohexylphosphine or tBuXPhos Pd G3, a base like for example $K_2CO_3$ or t-BuONa, in a solvent like for example DMF or THF.

Scheme 1-b

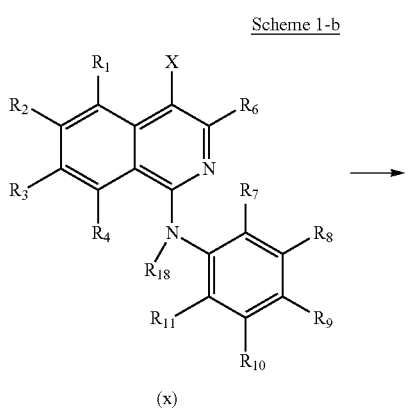

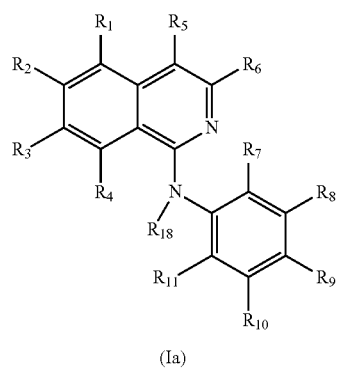

(Ia)

Other compounds of Formula (I), wherein Y is NH (Formula Ia) can also be synthesized from compounds of Formula (Ia) wherein $R^6$ is a halogen (Formula (xi)) as described in Scheme 1-b below.

Compounds of Formula (xi) wherein X can be Iodine, Bromide or Chlorine is reacted in a cross-coupling reaction with an organometallic reagent like for example a boronic acid or ester $R1B(OR)_2$ or an amine, in the presence of a catalyst/ligand system like for example $Pd(OAc)_2$/tricyclohexylphosphine or tBuXPhos Pd G3, a base like for example $K_2CO_3$ or t-BuONa, in a solvent like for example DMF or THF.

Scheme 1-c

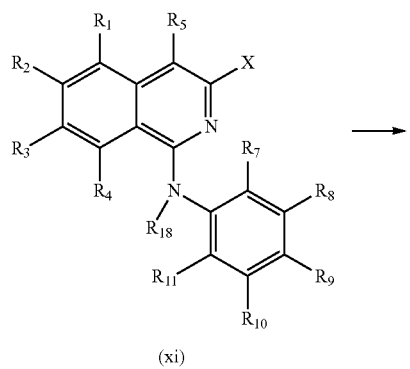

(xi)

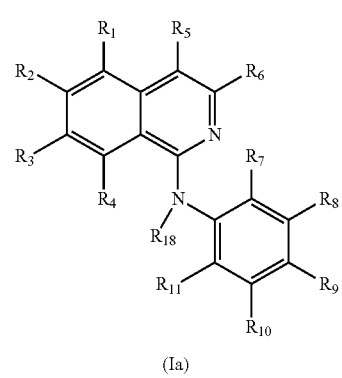

(Ia)

Intermediates of formula (i) wherein Z is a bromine or chlorine can be synthesized according to the Scheme 1-d below.

Isoquinolines (xii) can be reacted with an oxidizing agent like m-CPBA, in a solvent like for example DCM to obtain the N-oxide intermediate (xiii). Intermediate (xiii) can be then reacted with a halogenating agent like $POCl_3$ or $POBr_3$, to produce Intermediate (1).

Scheme 1-d

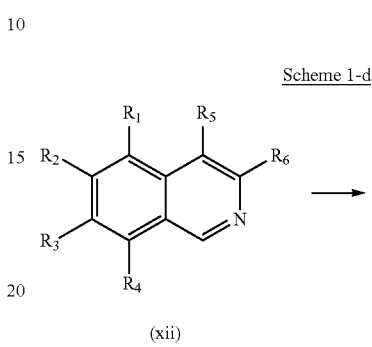

(xii)

(xiii)

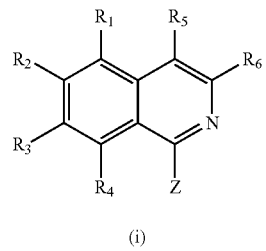

(i)

Compounds of Formula (I), wherein Y is $CH_2$ (Formula Ib) can be synthesized as described in Scheme 2 below.

An ethylamine intermediate of Formula (iv) is mixed with a phenyl acetic acid intermediate or a phenylacetyl chloride intermediate of Formula (v) and the mixture heated, e.g. at about 180° C. for about 2 h. Then after cooling, dichloromethane is added and the organic layer is washed by water. After extraction, e.g. with dichloromethane drying and evaporation under reduced pressure, intermediate amide compound of Formula (vi) is obtained. Compound of Formula (vi) is dissolved in a polar solvent such as toluene under heating, e.g. 90° C. and a solution of $POCl_3$ or $P_2O_5$ is added drop to drop and let reacted under heating, e.g. at about 100° C. for about 2 h. After cooling to room temperature and partial elimination of the solvent, warm water (e.g. 60° C.) is carefully added before stirring until complete solubilization.

Scheme 2

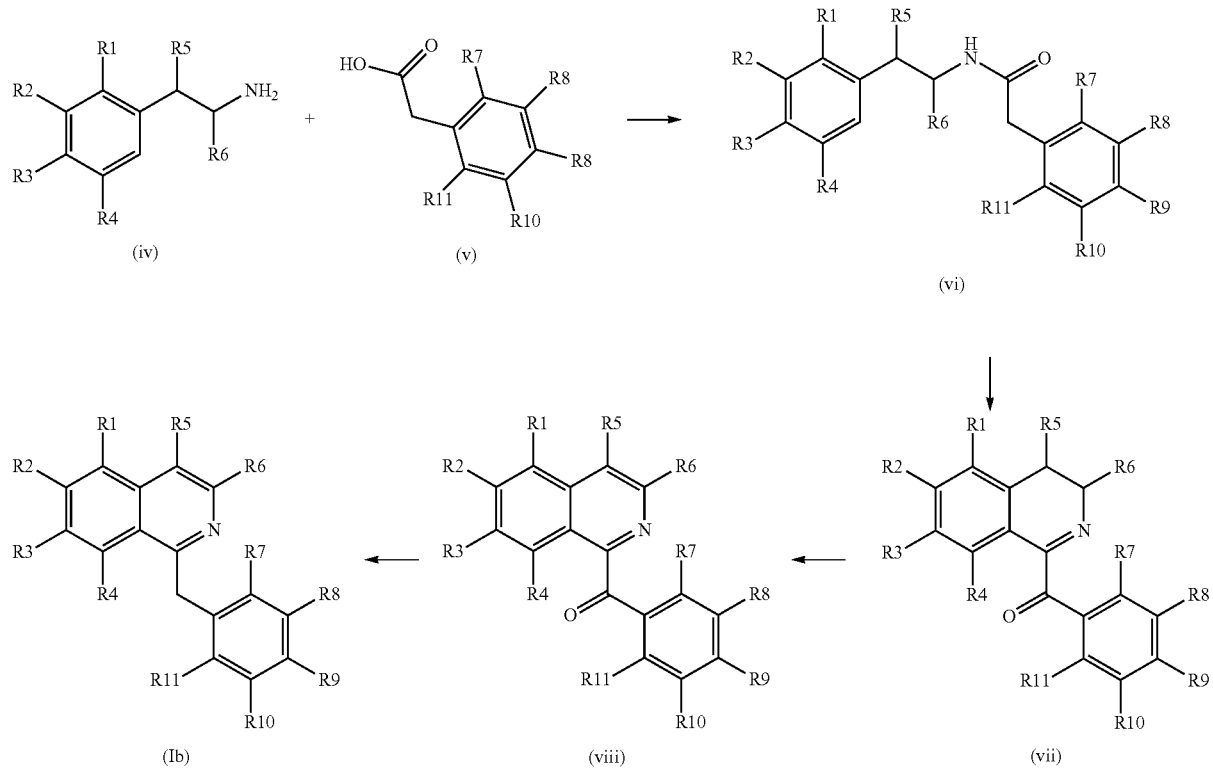

The aqueous phase was alkalized, e.g. with 20% NaOH, then extracted with an apolar solvent such as $CH_2Cl_2$ and dried on Magnesium sulfate. After elimination of solvent under reduce pressure, a dihydroisoquinoleine intermediate of Formula (vii) is obtained. $MnO_2$ and $Na_2SO_4$ are added to the dihydroisoquinoleine intermediate of Formula (vii) in a polar solvent such as toluene. The whole mixture is heated for about 2 h at reflux. After cooling and filtration, the crude is separated on silica gel to lead to a carbonyl intermediate of Formula (viii) or, alternatively, a dihydroisoquinoleine intermediate of Formula (vii) is subjected to heating in presence of sulfur or Pd/C to lead to a carbonyl intermediate of Formula (viii). This carbonyl intermediate is then reduced in glycol ethylene for example by the addition of hydrazine monohydrate or in presence of a hydride such as $NaBH_3CN$ in presence de $ZnCl_2$ or by catalytic hydrogenation ($H_2$ in presence of Pd/C in presence of acid) and whole mixture was heated for about 30 min at about 120° C. After, KOH in glycol ethylene is added and the whole mixture is heated for about 3 h at about 190° C. After cooling and extraction with an apolar solvent such as dichloromethane, the organic layer is washed successively by water and bride. After drying and evaporation under reduce pressure, the crude is separated on silica gel under nitrogen to lead to a compound of Formula (Iab).

According to one aspect, a compound according to Formula (I), wherein groups at least one group of $R^{16}$ to $R^{18}$ is different from H can be obtained N-alkylation of an intermediate of Formula (Ia) or by reduction of a carbonyl intermediate of Formula (vii) as described herein.

Patients

In an embodiment, patients according to the invention are subjects suffering from a disorder related to GLUT1-DS.

In a particular embodiment, patients according to the invention are suffering from GLUT1-DS.

In an embodiment, patients according to the invention are patients that are at risk of suffering from GLUT1-DS.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

Several methods for preparing the compounds of this invention are illustrated in the following Examples. Unless otherwise noted, all starting materials were obtained from commercial suppliers and used without further purification. Specifically, the following abbreviations in Table 1 may be used in the examples and throughout the specification:

TABLE 1

| | |
|---|---|
| ACN (acetonitrinile) | MTBE |
| $CDCl_3$ (deuterated chloroform) | $N_2$ (nitrogen gaz) |

TABLE 1-continued

| | |
|---|---|
| DCE (dichloroethane) | $NaHCO_3$ (sodium hydrogenocarbonate) |
| DCM (dichloromethane) | NaOAc (sodium acetate) |
| DMF (dimethylformamide) | NaOtBu (sodium tert-butoxide) |
| DMSO-d6 (deuterated dimethyl-sulfoxide) | $Na_2SO_4$ (sodium sulphate) |
| EtOAc (or EA: ethyl acetate) | Pd/C (palladium on charcoal) |
| EtOH (ethanol) | $Pd_2(dba)_3$ (palladium (II)dibenzyl-ideneacetone) |
| g (grams) | $PdCl_2(dppf)_2$ (Bis(1,1'-bis(diphenylphosphanyl) ferrocene palladium (II) dichloride) |
| $^1H$ (proton) | $Pd(PPh_3)_4$ (Tetrakis(triphenylphosphine) palladium(0)) |
| $H_2$ (hydrogen) | PE (Petroleum ether) |
| HCl (hydrochloric acid) | $POCl_3$ (Phosphorus trichloride) |
| HPLC (High Pressure Liquid Chromatography) | Prep-TLC (Preparative thin layer chromatography) |
| Hz (Hertz) | PyBrOP (Bromo-tris-pyrrolidino-phosphonium hexafluorophosphate) |
| $K_2CO_3$ (potassium carbonate) | RT (Retention Time) |
| $K_3PO_4$ (potassium phosphate) | $Bu_3PHBF_4$ (Tri-tert-butylphosphonium tetrafluoroborate) |
| LCMS (Liquid Chromatography Mass Spectrum) | tBuXPhos (2-di-tert-butylphosphino-2',4',6'-triisopropylbiphenyl) |
| m-CPBA (meta-chloroperbenzoic acid) | tBuXPhos Pd G3 (Methanesulfonato(2-di-t-butyl-phosphino-2',4',6'-tri-i-propyl-1,1'-biphenyl)(2'-amino-1,1'-biphenyl-2-yl)palladium(II)) |
| MeOH (methanol) | TFA (trifluoroacetic acid) |
| mg (milligrams) | THF (tetrahydrofuran) |
| MHz (megahertz) | Xantphos (4,5-Bis(diphenyl-phosphino)-9,9-dimethylxanthene) |
| µL(microliters) | XPhos (2-Dicyclohexylphosphino-2',4',6'-triisopropylbiphenyl) |
| mL (milliliters) | $Zn(CN)_2$ (zinc cyanide) |
| µmol (micromoles) | |
| mmol (millimoles) | |

Unless otherwise indicated, all temperatures are expressed in ° C. (degrees Celsius). All reactions are conducted not under an inert atmosphere at room temperature unless otherwise noted.

The following studies are conducted to support the effectiveness of compounds of the invention according to the invention.

Example 1: Synthesis of Compounds of the Invention

All synthetic reagents and solvents are used as is. If necessary, the solvents used in the reactions are previously dried and/or distilled in accordance with the state of the art. Some solvents are commercially available in an anhydrous state and are used as is.

Reactive Conditions

When anhydrous conditions are required, the glassware is first dried in an oven (T>100° C.). All reactions are performed under nitrogen atmosphere. The ambient temperature (rt) refers to 20-25° C. The reaction temperature of −78° C. is obtained by freezing a water bath of acetone with carboglace or liquid nitrogen. The temperature of 0° C. corresponds to the use of an ice water bath. For heating, an oil bath with a temperature sensor is used for temperature control. The progress of the reactions is controlled by thin layer chromatography (CCM). These CCM (DC Kieselgel 60 F254, UV254 plates) correspond to aluminium plates precoated with silica gel and UV fluorescent indicator. The plates are revealed under UV light (254 and 365 nm) or using a developer adapted to the molecules to be visualized. A phosphomolybdic acid solution is commonly used as an oxidizing developer with or without thermal revelation.

Purification Techniques

Flash Chromatography:

Silica gel (Kieselgel 60 from MN, 15-40 µm from Macherey-Nagel) is used in the purification of raw products by Flash chromatography. The samples are either deposited directly at the column head or applied as a solution in a silica gel suspension.

Automated Chromatography Flash:

The purification system used is a Combiflash Companion™ from Teledyne Isco. The raw samples are dissolved in a small amount of suitable solvent and applied to pre-conditioned RediSep® columns. These columns are placed in the Combiflash Companion purification system™ and purification is performed using a solvent gradient program. The system is used with an automated collector. The detection is carried out by UV or by the collection of all the fractions analysed by HPLC.

Nuclear Magnetic Resonance (NMR) Spectrometry:

NMR spectra are recorded using a Bruker UltraShield spectrometer operating at 400 MHz ($^1H$) and 100 MHz (13C). Spectrum calibration is performed by adding tetramethyl silane (TMS) to the deuterated solvent as the internal reference. The calibration is obtained by setting the 0 to the TMS signal.

For fluorine 19, CFCl3 is used as an external reference. Chemical displacements are reported in parts per million (ppm) and coupling constants are given in Hertz (Hz). Abbreviations for the multiplicity of proton and carbon signals are: s singlet, d doublet, dd doublet of doublet, dt doublet of triplets, ddt doublet of triplets, t triplet, tt triplet of triplets, q, quintet, m multiplet.

Mass Spectrometry (SM):

Mass spectra are performed using a Bruker Q-TOF maXis coupled to a Dionex Ultimate 3000 RSLC chain used in FIA (Flow Injection Analysis=without column) with an ACN/H2O+0.1% formic acid mixture 65/35 to 200 µL/min as the solvent. The injection volume is 0.2 µL. Most of the time, the analyses are performed in positive mode with the ESI source (Electrospray Ionisation).

Preparation of Samples:

The samples are taken at a concentration of about 1 mg/mL with the solvent then diluted approximately 500 times (≈2 ng/μL) in methanol (sometimes another solvent more appropriate according to the structure of the compound to be analyzed: water, acetonitrile . . . ). If the signal obtained is insufficient, the sample concentration is increased.

Melting Point Measurement:

Melting points are measured using a STUART SMP3.

High Performance Liquid Chromatography (HPLC):

HPLC analyses are performed on a Waters analytical HPLC system (Waters Delta 600 Multisolvent pump, Waters 600 system controller, Rheodyne 7725i injector with a 20 μl sample loop) controlled with Empower software and equipped with appropriate analytical column. The detection is carried out with a UV detector with photodiode strip (Waters 2996) and/or a refractometer.

Compounds 1 to 3 from Table 2 below of Formula (I), in particular (Ia) were synthesized according the Scheme 1 and compound 4 of Formula (I), in particular (Ib), according to Scheme 2.

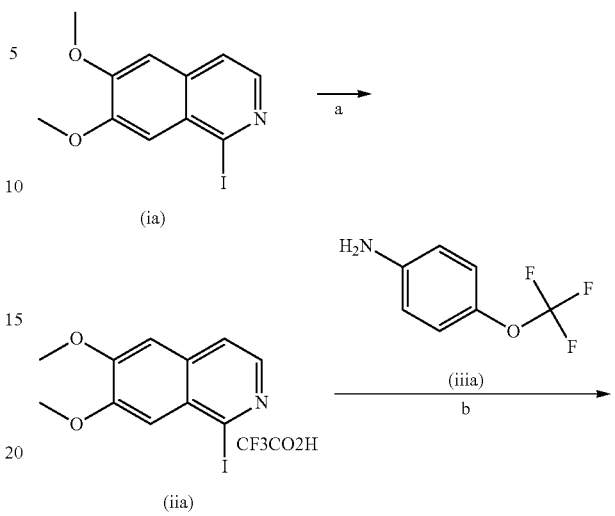

Scheme 3

TABLE 2

| Ex | Y | $R^1$ | $R^2$ | $R^3$ | $R^4$ | $R^5$ | $R^6$ | $R^7$ | $R^8$ | $R^9$ | $R^{10}$ | $R^{11}$ |
|---|---|---|---|---|---|---|---|---|---|---|---|---|
| 1 | NH | H | OCH$_3$ | OCH$_3$ | H | H | H | H | H | OCF$_3$ | H | H |
| 2 | NH | H | OCH$_3$ | OCH$_3$ | H | H | H | H | H | CF$_3$ | H | H |
| 3 | NH | H | H | H | H | H | H | H | H | OCF$_3$ | H | H |
| 4 | CH$_2$ | H | OCH$_3$ | OCH$_3$ | H | H | H | H | H | OCF$_3$ | H | H |
| 5 | NH | H | OCH$_3$ | OCH$_3$ | H | H | H | H | OCH$_3$ | OCH$_3$ | H | H |
| 6 | NH | H | OCH$_3$ | OCH$_3$ | H | H | H | H | H | CH$_3$ | H | H |
| 7 | NH | H | OCH$_3$ | OCH$_3$ | H | H | H | H | H | OCH$_3$ | H | H |
| 8 | NH | H | OCH$_3$ | OCH$_3$ | H | H | H | H | H | O(CH$_2$)$_2$OCH$_3$ | H | H |
| 9 | NH | H | OCH$_3$ | OCH$_3$ | H | H | H | H | H | CH$_2$OCH$_3$ | H | H |
| 10 | NH | H | OCH$_3$ | OCH$_3$ | H | H | H | F | H | OCF$_3$ | H | H |
| 11 | NH | H | OCH$_3$ | OCH$_3$ | H | H | H | H | OCF$_3$ | H | H | H |
| 12 | NH | H | OCH$_3$ | H | H | H | H | H | H | OCF$_3$ | H | H |
| 13 | NH | H | Cl | H | H | H | H | H | H | OCF$_3$ | H | H |
| 14 | NH | H | OCH$_3$ | OCH$_3$ | H | H | H | H | F | OCF$_3$ | H | H |
| 15 | NH | H | OCH$_3$ | OCH$_3$ | H | H | H | H | N(CH$_3$)$_2$ | H | H | H |
| 16 | NH | H | OCH$_3$ | OCH$_3$ | H | H | H | H | OCHF$_2$ | H | H | H |
| 17 | NH | H | OCH$_3$ | OCH$_3$ | H | H | H | CF$_3$ | H | CN | H | H |
| 18 | NH | H | OCH$_3$ | OCH$_3$ | H | H | H | H | H | SCH$_3$ | H | H |
| 19 | NH | H | OCH$_3$ | OCH$_3$ | H | H | H | H | Cl | OCF$_3$ | H | H |
| 20 | NH | H | OCH$_3$ | OCH$_3$ | H | H | H | H | H | (CH$_2$)$_2$OCH$_3$ | H | H |
| 21 | NH | CH$_3$ | OCH$_3$ | H | H | H | H | H | H | OCF$_3$ | H | H |
| 22 | NH | N(CH$_3$)$_2$ | OCH$_3$ | H | H | H | H | H | H | OCF$_3$ | H | H |
| 23 | NH | H | OCH$_3$ | H | H | Cl | H | H | H | OCF$_3$ | H | H |
| 24 | NH | H | OCH$_3$ | H | H | CH$_3$ | H | H | H | OCF$_3$ | H | H |
| 25 | NH | H | OCH$_3$ | H | H | Br | H | H | H | OCF$_3$ | H | H |
| 26 | NH | H | OCH$_3$ | H | H | H | Cl | H | H | OCF$_3$ | H | H |
| 27 | NH | H | N(CH$_3$)$_2$ | H | H | H | H | H | H | OCF$_3$ | H | H |
| 28 | NH | H | CN | H | H | H | H | H | H | OCF$_3$ | H | H |
| 29 | NH | H | COOCH$_3$ | H | H | H | H | H | H | OCF$_3$ | H | H |
| 30 | NH | H | CH$_2$CH$_3$ | H | H | H | H | H | H | OCF$_3$ | H | H | a) Preparation of 6,7-dimethoxy-N-(4-(trifluoromethoxy)phenyl)isoquinolin-1-amine (1)

Compound (1) was prepared as detailed in Scheme 3 below.

a. Iodized Salt Formation

Trifluoroacetic acid (34 μl) is added dropwise to an isoquinoline (ia) (@rtMolecules) (m=120 mg, 0.38 mmol) in isopropanol (2 ml). The whole is drawn under vacuum one night to lead to salt intermediate (iia).

-continued

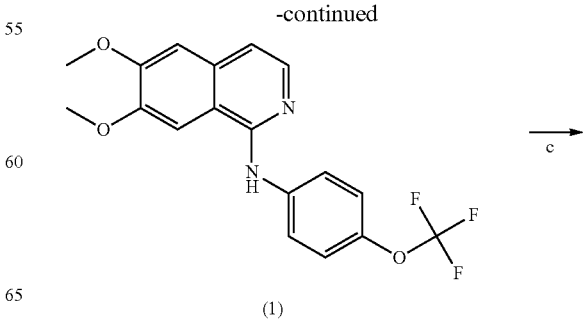

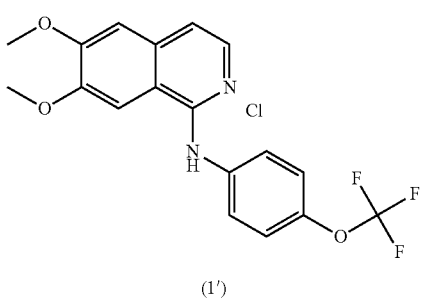

(1')

b. Introduction of Aniline to Form Compound (1)

To salt intermediate (iia) (m=61 mg, 0.19 mmol) in tert-butanol (v=1.4 ml), 4-trifluoromethoxyaniline (m=86 mg, 0.47 mmol) is added as intermediate (iiia) (AK Scientific (USA). The whole is refluxed overnight, then after cooling, hydrolysed with a saturated NaHCO$_3$ solution. After extraction with dichloromethane drying and evaporation, the crude is separated on silica gel (Eluant CH$_2$Cl$_2$/MeOH:97/3) to lead to compound of the invention (1) (m=55 mg, 79%).

c. Formation of Hydrochloride (1')

Compound (1) (m=55 mg, 0.16 mmol) is solubilized at 0° C. in an AcOEt/EtOH mixture (16/2, 5 ml) and HCl (2M, in ethyl acetate, 0.3 ml) added. After 15 minutes agitation, solvent is removed under reduced pressure to obtain compound of the invention (1') which was characterized as follows: $^1$H NMR (400 MHz, DMSO) δ(ppm) 12.67 (s, 1H), 11.37 (s, 1H), 8.35 (s, 1H), 7.71 (d, J=8.9 Hz, 2H), 7.59-7.44 (m, 4H), 7.32 (d, J=6.8 Hz, 1H), 4.01 (s, 3H), 3.99 (s, 3H). $^{13}$C NMR (101 MHz, DMSO) δ(ppm) 155.53, 151.04, 149.93, 135.67, 134.81, 127.93, 123.18, 121.84, 113.00, 112.97, 107.73, 105.96, 57.20, 56.73. DEPT 135 NMR (101 MHz, DMSO) δ 127.94, 123.19, 113.00, 107.73, 105.95, 57.20, 56.73.

b) Preparation of 6,7-dimethoxy-N-(4-(trifluoromethyl)phenyl)isoquinolin-1-amine (2) Compound (2) Was Prepared as Detailed in Scheme 4 Below a. Iodized Salt Formation The same protocol was used to obtain to salt intermediate (iia) as described above using the following amount: trifluoroacetic acid (71 µl) and isoquinoline (ia) (m=250 mg, 0.793 mmol) in isopropanol (4.2 ml).

b. Introduction of Aniline to Form Compound (2)

To salt intermediate (iia) (0.793 mmol) in tert-butanol (v=8 ml), 4-trifluoromethylaniline (m=320 mg, 1.98 mmol) is added as intermediate (iiib). The whole is refluxed overnight, then after cooling, the precipitate was solubilized in CH$_2$Cl$_2$ (250 ml)/NaHCO$_3$ saturated aqueous solution (250 ml) mixture. After extraction with dichloromethane (3×) and washing with NaCl saturated aqueous solution, the organic phase was drying before evaporation under reduce pressure. The crude is separated on silica gel (Eluant CH$_2$Cl$_2$/MeOH: 99/1) to lead to the compound of the invention (2) (m=161 mg, 58.2%).

Scheme 4

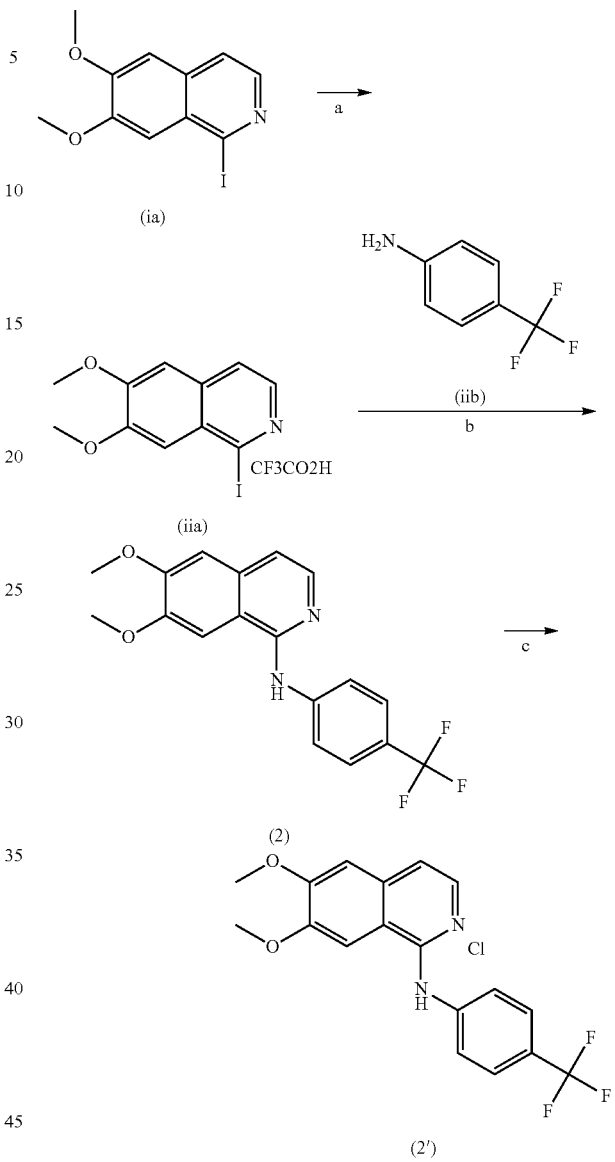

b. Introduction of Aniline to Form Compound (2)

To salt intermediate (iia) (0.793 mmol) in tert-butanol (v=8 ml), 4-trifluoromethylaniline (m=320 mg, 1.98 mmol) is added as intermediate (iiib). The whole is refluxed overnight, then after cooling, the precipitate was solubilized in CH$_2$Cl$_2$ (250 ml)/NaHCO$_3$ saturated aqueous solution (250 ml) mixture. After extraction with dichloromethane (3×) and washing with NaCl saturated aqueous solution, the organic phase was drying before evaporation under reduce pressure. The crude is separated on silica gel (Eluant CH$_2$Cl$_2$/MeOH: 99/1) to lead to the compound of the invention (2) (m=161 mg, 58.2%).

c. Formation of Hydrochloride (2')

Compound (2) (m=161 mg, 0.462 mmol) is solubilized at 0° C. in an AcOEt (3.2 ml) and HCl (0.4M in ethyl acetate, 1.2 ml) added. After 15 minutes agitation, solvent is removed under reduced pressure to obtain compound of the invention (2') which was characterized as follows:

$^1$H NMR (400 MHz, DMSO) δ(ppm) 13.04 (s, 1H), 11.91 (s, 1H), 8.53 (s, 1H), 7.91 (d, J=8.5 Hz, 2H), 7.81 (d, J=8.4

Hz, 2H), 7.57 (t, J=3.4 Hz, 2H), 7.39 (d, J=6.8 Hz, 1H), 4.04 (s, 3H), 4.00 (s, 3H). $^{13}$C NMR (101 MHz, DMSO) δ(ppm) 155.82, 151.15, 149.27, 140.82, 135.22, 127.54, 127.50, 127.31, 125.64, 113.68, 113.48, 107.69, 106.57, 57.38, 56.78. DEPT 135 NMR (101 MHz, DMSO) δ(ppm) 127.54, 127.50, 127.32, 125.64, 113.68, 107.69, 106.57, 57.38, 56.78.

c) Preparation of N-(4-(trifluoromethoxy)phenyl)isoquinolin-1-amine (3)

Compound (3) was prepared as detailed in Scheme 5 below:

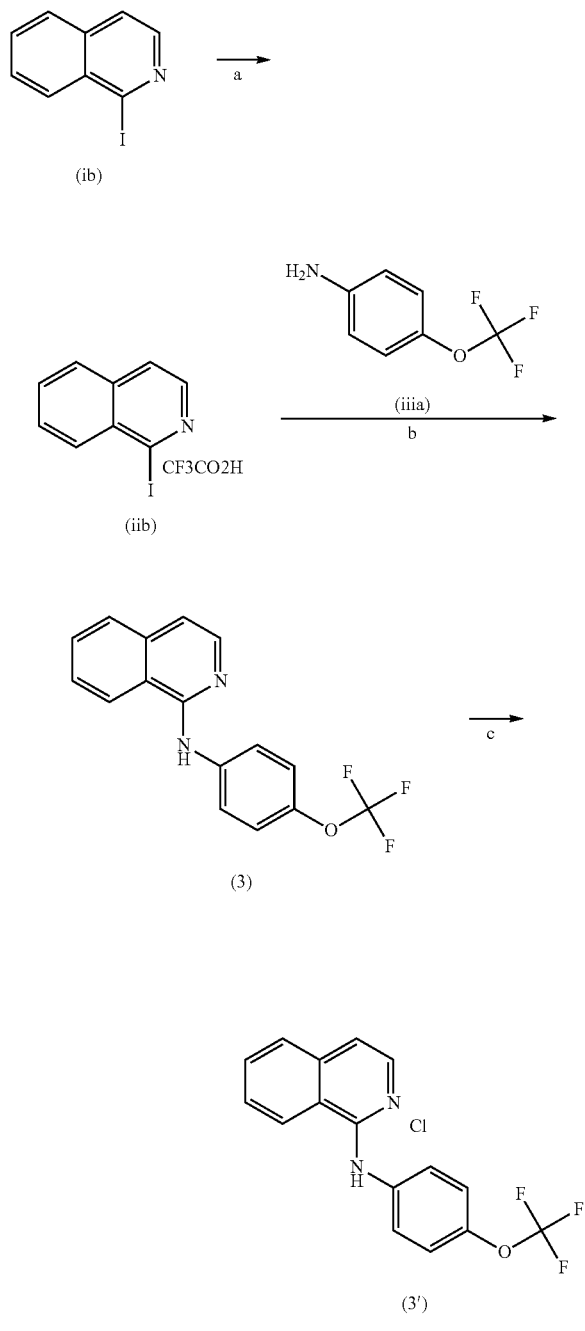

a. Iodized Salt Formation

Trifluoroacetic acid (0.46 ml) is added dropwise to an isoquinoline (ib) (TCI Europe) (m=1.3 g, 5.11 mmol) in isopropanol (27 ml). The whole is drawn under vacuum one night to lead to intermediate (iib).

b. Introduction of Aniline to Form Compound (3)

To salt intermediate (iib) (5.11 mmol) in tert-butanol (v=50 ml), 4-trifluoromethoxyaniline (AK Scientific (USA)) (1.73 ml, 10.22 mmol) is added as intermediate (iiia). The whole is refluxed overnight, then after cooling, the precipitate was solubilized in $CH_2Cl_2$ (250 ml)/ $NaHCO_3$ saturated aqueous solution (250 ml) mixture. After extraction with dichloromethane (3×) and washing with NaCl saturated aqueous solution, the organic phase was drying before evaporation under reduce pressure. The crude is separated on silica gel (Eluant EP/AcOEt: 5/95) to lead to compound of the invention (3) (m=1.2 g, 64%).

c. Formation of Hydrochloride (3')

Compound (3) (m=200 mg, 0.657 mmol) is solubilized at 0° C. in an AcOEt/EtOH mixture (4.6 ml) and HCl (0.4M, in ethyl acetate, 1.7 ml) added. After 15 minutes agitation, solvent is removed under reduced pressure to obtain compound of the invention (3') which was characterized as follows: $^1$H NMR (400 MHz, DMSO) δ(ppm) 12.81 (s, 1H), 11.70 (s, 1H), 9.04 (d, J=8.2 Hz, 1H), 8.23-7.92 (m, 2H), 7.92-7.81 (m, 1H), 7.76 (d, J=8.5 Hz, 2H), 7.64 (d, J=6.6 Hz, 1H), 7.57 (d, J=8.2 Hz, 2H), 7.41 (d, J=6.7 Hz, 1H). $^{13}$C NMR (101 MHz, DMSO) δ(ppm) 152.03, 137.71, 135.41, 134.89, 129.12, 128.11, 126.32, 123.13, 119.01, 113.43, 67.48, 25.59. DEPT 135 NMR (101 MHz, DMSO) δ(ppm) 134.88, 129.12, 128.11, 126.32, 123.14, 113.43, 67.48, 25.59.

d) Preparation of 6,7-dimethoxy-1-(4-(trifluoromethoxy)benzyl)isoquinoline (4)

Compound (4) was prepared as detailed in Scheme 6 below.

a. Amide Formation 2-(3,4-dimethoxyphenyl)ethanamine intermediate of Formula (iva) (TCI Europe) (m=2 g, 11 mmol) and 2-(4-(trifluoromethoxy)phenyl)acetic acid intermediate of Formula (va) (Fluorochem (UK)) (m=2.4 g, 11 mmol) are heated at 180° C. until 2 h. Then after cooling, dichloromethane was added and the organic layer is washed by water. After drying and evaporation under reduce pressure, intermediate amide compound of Formula (via) was obtain (m=900 mg—21%).

b. Bishler Napieralski (BN) Reaction

To intermediate amide compound of Formula (via) (m=87 0 mg, 2.27 mmol) in toluene (v=15 ml) at 90° C., a solution of $POCl_3$ (1.5 ml) was added drop to drop. The whole was heated 2 h at 100° C. After cooling to room temperature and partial elimination of toluene, warm (60° C.) water (30 ml) was carefully added before stirring until complete solubilization. The aqueous phase was alkalized with 20% NaOH then extracted with $CH_2Cl_2$ and dried on Magnesium sulfate. After elimination of solvent under reduce pressure, a dihydroisoquinoline intermediate of Formula (viia) is obtained (m=750 mg—90%) characterized as follows: $^1$H NMR (400 MHz, $CDCl_3$) δ(ppm) 7.33 (d, J=8.4 Hz, 2H), 7.13 (d, J=8.5 Hz, 2H), 6.91 (s, 1H), 6.69 (s, 1H), 4.08 (s, 2H), 3.90 (s, 3H), 3.78-3.67 (m, 5H), 2.73-2.60 (m, 2H).

Scheme 6

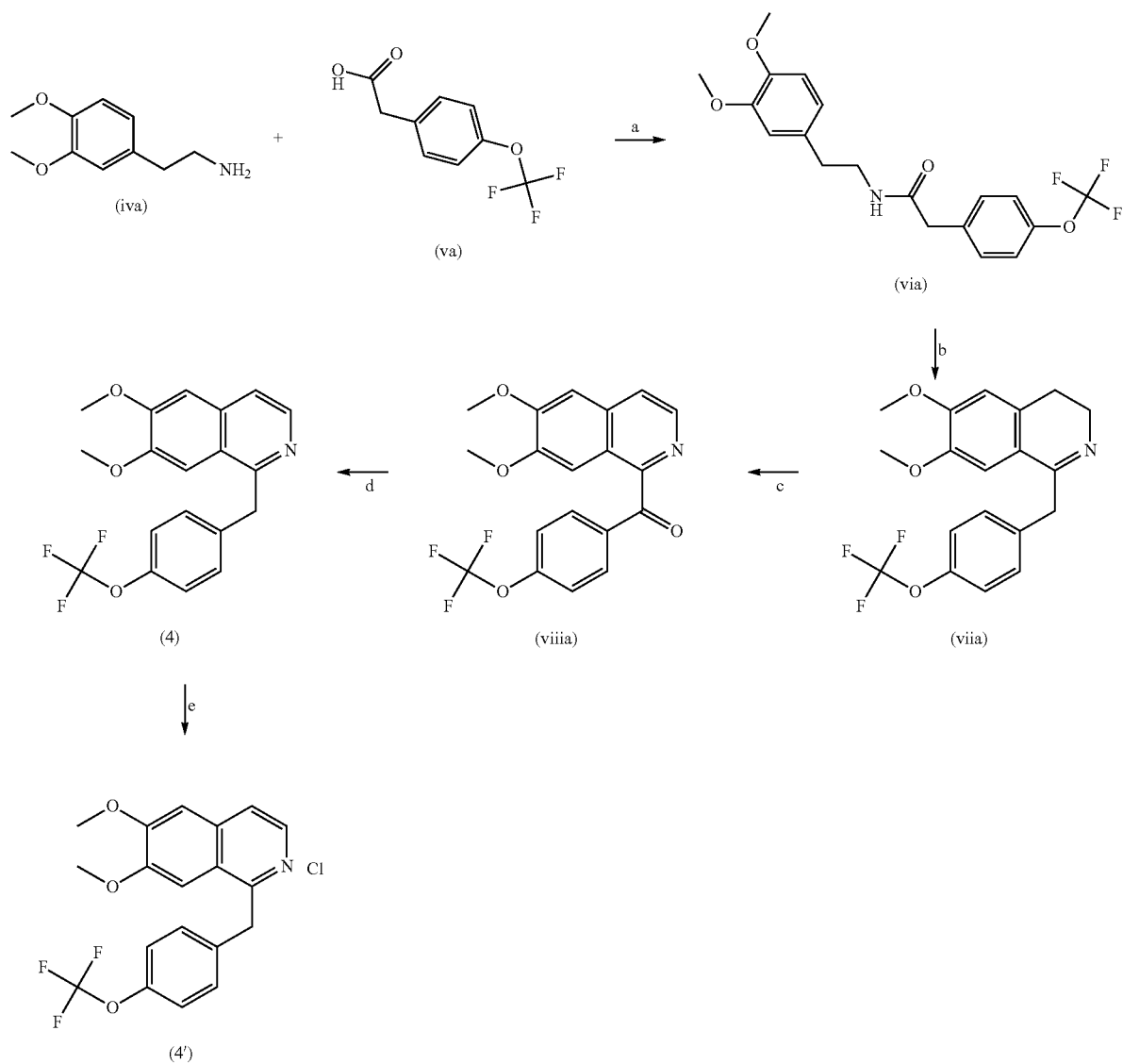

c. Oxidation Aromatization Reaction

To the dihydroisoquinoline intermediate of Formula (viia) (m=750 mg, 2.0 mmol) in toluene (18 ml) were added $MnO_2$ (3.7 g, 42.6 mmol) and $Na_2SO_4$ (4.5 g, 31.7 mmol). The whole is heated 2 h at reflux. After cooling and filtration, the crude is separated on silica gel (Eluent $CH_2Cl_2$/MeOH— 99/1) to lead to a carbonyl intermediate of Formula (viiia) (m=270 mg, 35%) characterized as follows: $^1H$ NMR (400 MHz, $CDCl_3$) δ(ppm) 8.47 (d, J=5.5 Hz, 3H), 8.05 (d, J=8.9 Hz, 6H), 7.73 (s, 2H), 7.69 (s, 2H), 7.32 (dd, J=8.9, 0.9 Hz, 6H), 7.27 (s, 2H), 7.16 (s, 3H), 4.07 (s, 9H), 4.00 (s, 9H).

d. Carbonyl Reduction

To carbonyl intermediate of Formula (vii) (m=270 mg, 0.71 mmol) in glycol ethylene (10 ml) was added hydrazine monohydrate (0.15 ml, 3.1 mmol). The whole was heated 30 min at 120° C. After KOH (320 mg—5.7 mmol) in glycol ethylene (2.5 ml) was added. The whole was heated 3 h at 190° C. After cooling and extraction with dichloromethane (3×3 5 ml), the organic layer is washed successively by water and bride. After drying and evaporation under reduce pressure, the crude is separated on silica gel under nitrogen (Eluant $CH_2Cl_2$/MeOH: 99/1) to lead to compound of the invention (4) (m=136 mg, 52.8%).

e. Hydrochloride Formation

β-carboline compound (4) (m=130 mg, 0.36 mmol) is solubilized at 0° C. in an AcOEt (3 ml) and HCl (2M, in ethyl acetate, 1 ml) added. After 15 minutes agitation, solvent is removed under reduced pressure to lead to compound of the invention (4') (110 mg—76.4%) characterized as follows: $^1H$ NMR (400 MHz, DMSO) δ(ppm) 8.43 (d, J=6.5 Hz, 1H), 8.19 (d, J=6.5 Hz, 1H), 7.84 (s, 1H), 7.78 (s, 1H), 7.68 (d, J=8.7 Hz, 2H), 7.34 (d, J=8.0 Hz, 2H), 5.10 (s, 2H), 4.04 (s, 3H), 4.00 (s, 3H). $^{13}C$ NMR (101 MHz, DMSO) δ(ppm) 157.00, 153.80, 152.65, 147.82, 137.16, 136.39, 131.24, 130.30, 122.46, 122.32, 121.89, 107.20, 105.75, 57.15, 56.99, 35.10. DEPT 135 NMR (101 MHz, DMSO) δ(ppm) 131.24, 130.30, 122.46, 121.89, 107.20, 105.75, 57.16, 56.99, 35.10.

Preparation of N-(3,4-dimethoxyphenyl)-6,7-dimethoxyisoquinolin-1-amine (5)

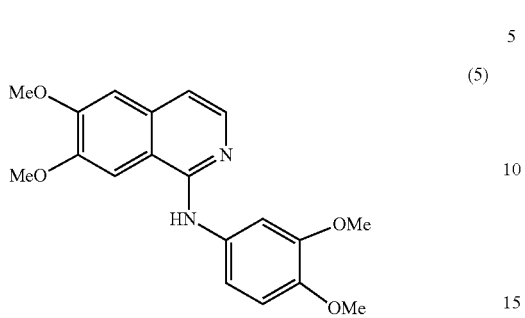

Compound (5) was prepared according to Scheme 1 as described for (1), starting from intermediate (iia) (163 mg, 0.38 mmol) and 3,4-dimethoxyaniline (146 mg, 0.95 mmol) to provide (5) (90 mg) as yellow solid. $^1$H-NMR (400 MHz, DMSO-d6) δ(ppm) 12.18 (s, 1H), 11.20 (s, 1H), 7.53 (s, 1H), 7.43 (d, J=6.8 Hz, 1H), 7.23 (d, J=6.9 Hz, 1H), 7.17 (dd, J=9.2, 5.4 Hz, 2H), 7.05 (dd, J=8.5, 2.0 Hz, 1H), 3.99 (s, 3H), 3.98 (s, 3H), 3.84 (s, 3H), 3.78 (s, 3H).

Preparation of 6,7-dimethoxy-N-(p-tolyl)isoquinolin-1-amine (6)

Compound (6) was prepared as detailed in Scheme 7 below.

Scheme 7

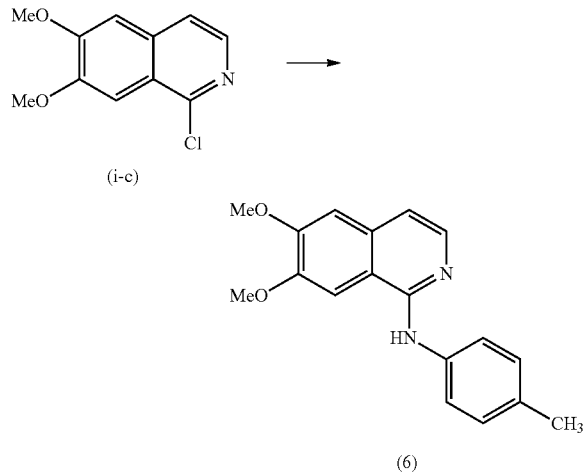

Intermediate (i-c) was prepared as detailed in the Scheme 7-a below:

Scheme 7-a

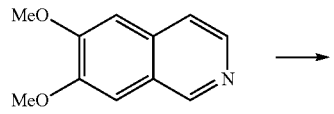

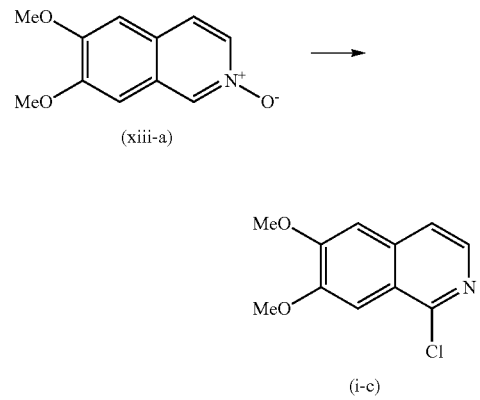

To a solution of 6,7-dimethoxyisoquinoline (9 g, 47.57 mmol) in DCM (150 mL) was added 3-chlorobenzenecarboperoxoic acid (15.45 g, 76.11 mmol, 85% purity) in portions at 20° C. The mixture was stirred at 20° C. for 12 hours. The residue was dropped into a saturated $K_2CO_3$ aqueous solution (60 ml). The resulting mixture was adjusted to pH=9-10 with saturated $K_2CO_3$ aqueous solution. The mixture was extracted with dichloromethane (20 ml×20), the combined organic layers was dried with anhydrous $Na_2SO_4$ and concentrated under reduced pressure to give Intermediate (xiii-a) (6.3 g, yield 58%) as grey solid.

Intermediate (xiii-a) (6.2 g, 27.19 mmol, 90% purity) was added to $POCl_3$ (86 mL) in portions at 20° C. The mixture was stirred at 80° C. for 2 hours. The reaction mixture was concentrated and the residue was poured into water (200 ml). The resulting mixture was adjusted to pH=9-10 with a saturated $K_2CO_3$ solution, and extracted with ethyl acetate (3×100 ml). The combined organic layers were washed with brine (50 ml) and dried over anhydrous $Na_2SO_4$ and concentrated to give the crude product. The crude was purified by column chromatography ($SiO_2$, ethyl acetate/petroleum ether=15%) to give Intermediate (i-c) (4.3 g, yield 63.6%) as white solid. $^1$H NMR (400 MHz, DMSO-d6) δ(ppm) 3.96 (d, J=4.75 Hz, 6H) 7.43 (s, 1H) 7.47 (s, 1H) 7.71 (d, J=5.50 Hz, 1H) 8.12 (d, J=5.50 Hz, 1H).

Compound (6) was prepared according to Scheme 7: To a solution of Intermediate (i-c) (300 mg, 1.21 mmol) in THF (2 mL) was added p-toluidine (129.36 mg, 1.21 mmol), NaOBu-t (232.03 mg, 2.41 mmol), Xantphos (139.70 mg, 241.44 μmol), and $Pd_2(dba)_3$ (110.55 mg, 120.72 umol) at 20° C. under $N_2$ atmosphere. The mixture was stirred at 80° C. for 2 hours. The mixture was diluted with ethyl acetate (10 mL) and water (10 mL). The aqueous phase was extracted with ethyl acetate (3×10 mL). The organic layer was dried with brine (15 mL), dried with $Na_2SO_4$, filtered and concentrated under reduced pressure to give a crude product. The crude product was purified by prep-HPLC and then adjusted to pH 9 with solid $NaHCO_3$. The aqueous phase was extracted with ethyl acetate (3×20 mL). The organic layer was dried with $Na_2SO_4$, filtered and concentrated under reduced pressure to give (6) (68.2 mg, yield 19%) as light pink solid. $^1$H NMR (400 MHz, DMSO-d6) δ(ppm) 2.28 (s, 3H), 3.90 (s, 3H), 3.95 (s, 3H), 7.03 (d, J=5.51 Hz, 1H), 7.12 (d, J=8.16 Hz, 2H), 7.22 (s, 1H), 7.66 (d, J=8.38 Hz, 2H), 7.76-7.86 (m, 2H), 8.78 (s, 1H).

Preparation of 6,7-dimethoxy-N-(4-methoxyphenyl)isoquinolin-1-amine (7)

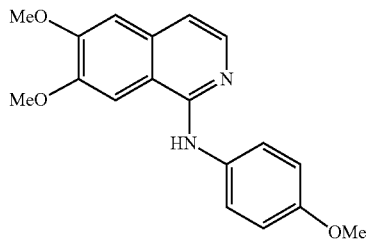
(7)

Compound (7) was prepared according to Scheme 7 as described for (6), starting from (i-c) (300 mg, 1.21 mmol) and 4-methoxyaniline (148.67 mg, 1.21 mmol) to provide (7) (46.4 mg, yield 12%) as light brown solid. $^1$H-NMR (400 MHz, DMSO-d6) δ(ppm) 3.75 (s, 3H) 3.85-3.98 (m, 6H) 6.91 (br d, J=8.88 Hz, 2H) 6.99 (d, J=5.63 Hz, 1H) 7.20 (s, 1H) 7.63 (br d, J=8.88 Hz, 2H) 7.73-7.82 (m, 2H) 8.73 (s, 1H).

Preparation of 6,7-dimethoxy-N-(4-(2-methoxyethoxy)phenyl)isoquinolin-1-amine (8)

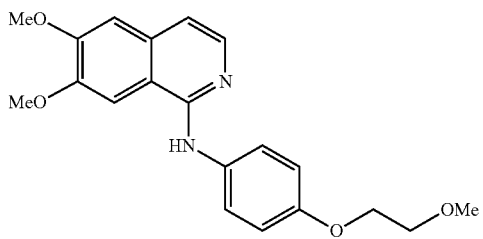 [SMILES: COCCOc1ccc(Nc2nccc3cc(OC)c(OC)cc23)cc1]

Compound (8) was prepared according to Scheme 7 as described for (6), starting from (i-c) (300 mg, 1.21 mmol) and 4-(2-methoxyethoxy)aniline (201.85 mg, 1.21 mmol) to provide (8) (148.2 mg, yield 34.6%) as pink solid. $^1$H NMR (400 MHz, DMSO-d6) δ(ppm) 3.32 (s, 3H), 3.63-3.68 (m, 2H), 3.90 (s, 3H), 3.95 (s, 3H), 4.04-4.09 (m, 2H), 6.92 (d, J=9.04 Hz, 2H), 6.99 (d, J=5.73 Hz, 1H), 7.20 (s, 1H), 7.63 (d, J=9.04 Hz, 2H), 7.72-7.80 (m, 2H), 8.73 (s, 1H).

Preparation of 6,7-dimethoxy-N-(4-(methoxymethyl)phenyl)isoquinolin-1-amine (9)

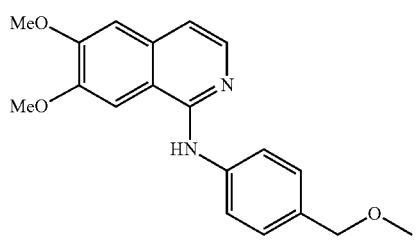
(9)

Compound (9) was prepared according to Scheme 7 as described for (6), starting from (i-c) (300 mg, 1.21 mmol) and 4-(methoxymethyl)aniline (165.60 mg, 1.21 mmol) to provide (9) (50 mg, yield 12.4%) was obtained as light pink solid. $^1$H NMR (400 MHz, DMSO-d6) δ(ppm) 3.28 (s, 3H), 3.91 (s, 3H), 3.96 (s, 3H), 4.36 (s, 2H), 7.07 (d, J=5.73 Hz, 1H), 7.21-7.28 (m, 3H), 7.77 (d, J=8.82 Hz, 3H), 7.84 (d, J=5.51 Hz, 1H), 8.88 (s, 1H).

Preparation of N-(2-fluoro-4-(trifluoromethoxy)phenyl)-6,7-dimethoxyisoquinolin-1-amine (10)

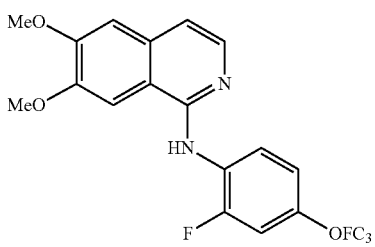
(10)

Compound (10) was prepared according to Scheme 7, as described for (6), starting from (i-c) (300 mg, 1.21 mmol) and 2-fluoro-4-(trifluoromethoxy)aniline (235.54 mg, 1.21 mmol) to provide (10) (246.5 mg, yield 51.9%) as white solid. $^1$H NMR (400 MHz, DMSO-d6) δ(ppm) 3.93 (d, J=13.13 Hz, 6H) 7.09 (d, J=5.63 Hz, 1H) 7.20-7.28 (m, 2H) 7.43 (br d, J=10.88 Hz, 1H) 7.65 (t, J=8.82 Hz, 1H) 7.71-7.80 (m, 2H) 8.87 (s, 1H).

Preparation of 6,7-dimethoxy-N-(3-(trifluoromethoxy)phenyl)isoquinolin-1-amine (11)

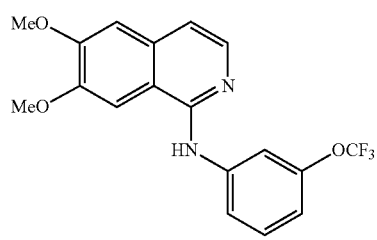 [SMILES: COc1cc2ccnc(Nc3cccc(OC(F)(F)F)c3)c2cc1OC]

Compound (11) was prepared according to Scheme 7, as described for Example (6), starting from (i-c) (300 mg, 1.21 mmol) and 3-(trifluoromethoxy)aniline (235.21 mg, 1.33 mmol) to provide (11) (205 mg, yield 45%) as a light yellow solid. $^1$H NMR (400 MHz, DMSO-d6) δ(ppm) 3.92 (s, 3H) 3.97 (s, 3H) 6.91 (dt, J=8.22, 1.04 Hz, 1H) 7.16 (d, J=5.65 Hz, 1H) 7.28 (s, 1H) 7.42 (t, J=8.22 Hz, 1H) 7.77 (s, 1H) 7.83 (dd, J=8.41, 1.25 Hz, 1H) 7.91 (d, J=5.65 Hz, 1H) 7.98 (s, 1H) 9.12 (s, 1H).

Preparation of 6-methoxy-N-(4-(trifluoromethoxy) phenyl)isoquinolin-1-amine (12)

Compound (12) was prepared as detailed in Scheme 8 below.

Scheme 8

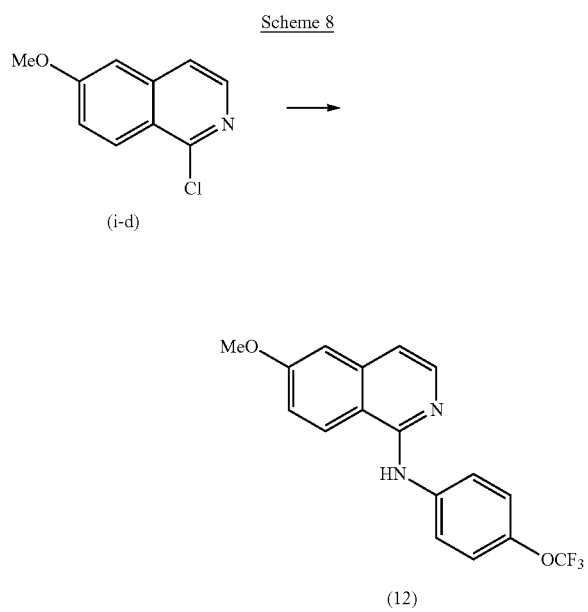 [SMILES: COc1ccc2c(Cl)nccc2c1 ; COc1ccc2c(Nc3ccc(OC(F)(F)F)cc3)nccc2c1]

Preparation of Intermediate (i-d)

Intermediate (i-d) was prepared according to Scheme 7-a as described for (i-c), starting from 6-methoxyisoquinoline (200 mg, 1.14 mmol) to provide (i-d) (300 mg, 1.47 mmol, yield 64%) as white solid. $^1$H NMR (400 MHz, DMSO-d6) δ(ppm) 3.93 (s, 3H) 7.40 (dd, J=9.26, 2.50 Hz, 1H) 7.46 (d, J=2.50 Hz, 1H) 7.76 (d, J=5.63 Hz, 1H) 8.14 (d, J=9.26 Hz, 1H) 8.20 (d, J=5.75 Hz, 1H).

Compound (12) was prepared according to Scheme 8 as described for (6), starting from (i-d) (300 mg, 1.24 mmol) and 4-(trifluoromethoxy)aniline (241.50 mg, 1.36 mmol) to provide (12) (80 mg, 227.35 μmol, yield 18.3%) as off-white solid. $^1$H NMR (400 MHz, DMSO-d6) δ(ppm) 7.14 (d, J=5.75 Hz, 1H) 7.18-7.32 (m, 4H) 7.89-7.99 (m, 3H) 8.42 (d, J=8.88 Hz, 1H) 9.20 (s, 1H).

Preparation of 6-chloro-N-(4-(trifluoromethoxy) phenyl)isoquinolin-1-amine (13)

Compound (13) was prepared as detailed in Scheme 9 below.

Scheme 9

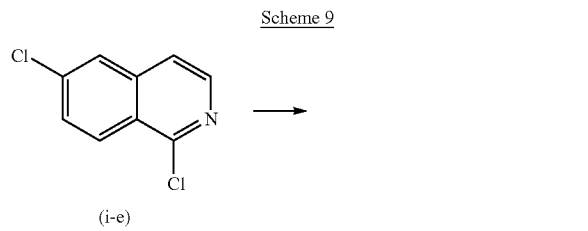

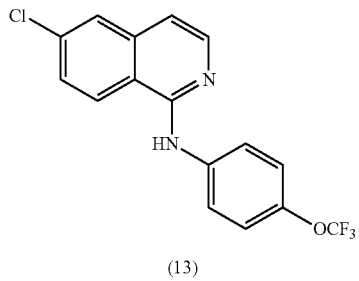

Preparation of Intermediate (i-e)

Intermediate (i-e) was prepared according to Scheme 7-a as described for (i-c), starting from 6-chloroisoquinoline (0.4 g, 2.23 mmol) to provide (i-e) (440 mg, 2.22 mmol, yield 99.8%) as brown solid. This product was used for next step directly.

Preparation of Example (13)

Compound (13) was prepared according to Scheme 9 as described for (6), starting from (i-e) (440 mg, 2.22 mmol) and 4-(trifluoromethoxy)aniline (472.21 mg, 2.67 mmol) to provide (13) (200 mg, 578.66 umol, yield 26%) as light yellow solid. $^1$H NMR (400 MHz, DMSO-d6) δ(ppm) 7.22 (d, J=5.75 Hz, 1H) 7.34 (br d, J=8.50 Hz, 2H) 7.68 (dd, J=9.01, 2.13 Hz, 1H) 7.95-8.02 (m, 3H) 8.05 (d, J=5.75 Hz, 1H) 8.58 (d, J=9.00 Hz, 1H) 9.44 (s, 1H).

Preparation of N-(3-fluoro-4-(trifluoromethoxy) phenyl)-6,7-dimethoxyisoquinolin-1-amine (14)

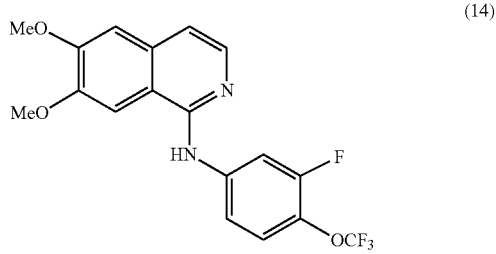 [SMILES: COc1cc2ccnc(Nc3ccc(OC(F)(F)F)c(F)c3)c2cc1OC]

Compound (14) was prepared according to Scheme 7 as described for (6), starting from (i-c) (300 mg, 1.21 mmol) and 3-fluoro-4-(trifluoromethoxy)aniline (235.54 mg, 1.21 mmol) to provide (14) (217.3 mg, yield 46%) as light green solid. $^1$H NMR (400 MHz, DMSO-d6) δ(ppm) 3.88-4.03 (m, 6H) 7.19 (d, J=5.63 Hz, 1H) 7.29 (s, 1H) 7.43-7.53 (m, 1H) 7.65 (dd, J=9.13, 1.13 Hz, 1H) 7.77 (s, 1H) 7.93 (d, J=5.63 Hz, 1H) 8.14 (dd, J=13.88, 2.50 Hz, 1H) 9.22(s,1H).

Preparation of N¹-(6,7-dimethoxyisoquinolin-1-yl)-N³,N³-dimethylbenzene-1,3-diamine (15)

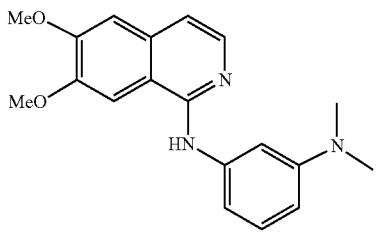
(15)

Compound (15) was prepared according to Scheme 7 as described for (6), starting from (i-c) (0.3 g, 1.34 mmol) and N¹,N¹-dimethylbenzene-1,3-diamine (219 mg, 1.6 mmol) to provide (15) (56 mg, yield 12%) as off white solid. $^1$H NMR (400 MHz, DMSO-d6) δ(ppm) 2.90 (s, 6H) 3.90 (s, 3H) 3.96 (s, 3H) 6.36-6.41 (m, 1H) 7.03 (d, J=5.63 Hz, 1H) 7.07-7.12 (m, 1H) 7.14-7.20 (m, 2H) 7.22 (s, 1H) 7.76 (s, 1H) 7.83 (d, J=5.63 Hz, 1H) 8.69 (s, 1H).

Preparation of N-(3-(difluoromethoxy)phenyl)-6,7-dimethoxyisoquinolin-1-amine (16)

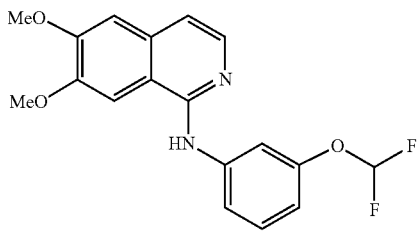
(16)

Compound (16) was prepared according to Scheme 7 as described for (6), starting from (i-c) (0.3 g, 1.34 mmol) and 3-(2,2-difluoroethyl)aniline (256 mg, 1.6 mmol) to provide (16) (99.5 mg, yield 21%) as white solid. $^1$H NMR (400 MHz, DMSO-d6) δ(ppm) 2.07 (s, 1H) 3.91 (s, 3H) 3.97 (s, 3H) 6.75 (dd, J=8.00, 2.13 Hz, 1H) 7.02 (s, 1H) 7.14 (d, J=5.63 Hz, 1H) 7.21 (s, 1H) 7.27 (s, 1H) 7.32 (s, 1H) 7.34 (s, 1H) 7.36 (s, 1H) 7.39 (s, 1H) 7.66-7.71 (m, 1H) 7.75-7.80 (m, 2H) 7.90 (d, J=5.63 Hz, 1H) 9.02 (s, 1H).

Preparation of 4-((6,7-dimethoxyisoquinolin-1-yl)amino)-3-(trifluoromethyl)benzo-nitrite (17)

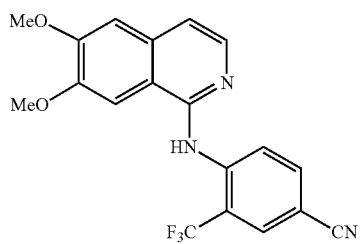
(17)

Compound (17) was prepared according to Scheme 7 as described for (6), starting from (i-c) (0.3 g, 1.34 mmol) and 4-amino-3-(trifluoromethyl)benzonitrile (299 mg, 1.6 mmol) to provide (17) (95 mg, yield 19%) as white solid. $^1$H NMR (400 MHz, DMSO-d6) δ(ppm) 3.78-3.96 (m, 6H) 6.44 (br d, J=6.13 Hz, 1H) 6.85-6.94 (m, 1H) 7.13 (br s, 1H) 7.19-7.26 (m, 1H) 7.27-7.37 (m, 1H) 7.55 (s, 1H) 7.67-7.79 (m, 1H) 7.86-8.04 (m, 2H) 8.06-8.14 (m, 1H) 8.23 (s, 1H) 8.77 (br s, 1H) 10.42 (br s, 1H).

Preparation of 6,7-dimethoxy-N-(4-(methylthio)phenyl)isoquinolin-1-amine (18)

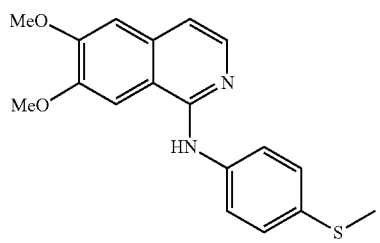
(18)

Compound (18) was prepared according to Scheme 7 as described for (6), starting from (i-c) (0.3 g, 1.34 mmol) and 4-(methylthio)aniline (224 mg, 1.6 mmol) to provide (18) (43 mg, yield 9.8%) as light yellow solid. $^1$H NMR (400 MHz, DMSO-d6) δ(ppm) 2.46 (s, 3H) 3.88-3.93 (m, 3H) 3.96 (s, 3H) 7.07 (d, J=5.75 Hz, 1H) 7.21-7.29 (m, 3H) 7.74-7.80 (m, 3H) 7.84 (d, J=5.63 Hz, 1H) 8.88 (s, 1H).

Preparation of N-(3-chloro-4-(trifluoromethoxy)phenyl)-6,7-dimethoxyisoquinolin-1-amine (19)

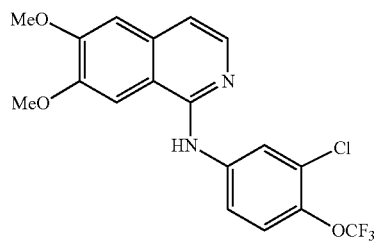
(19)

Compound (19) was prepared according to Scheme 7 as described for (6), starting from (i-c) (0.3 g, 1.34 mmol) and 3-chloro-4-(trifluoromethoxy)aniline (340 mg, 1.6 mmol) to provide (19) (110 mg, yield 20.6%) as white solid. $^1$H NMR (400 MHz, DMSO-d6) δ(ppm) 3.90-3.96 (m, 3H) 3.99 (s, 3H) 7.20 (d, J=5.63 Hz, 1H) 7.31 (s, 1H) 7.49-7.55 (m, 1H) 7.78 (s, 1H) 7.89-7.96 (m, 2H) 8.24 (d, J=2.50 Hz, 1H) 9.19 (s, 1H).

Preparation of 6,7-dimethoxy-N-(4-(2-methoxy-ethyl)phenyl)isoquinolin-1-amine (20)

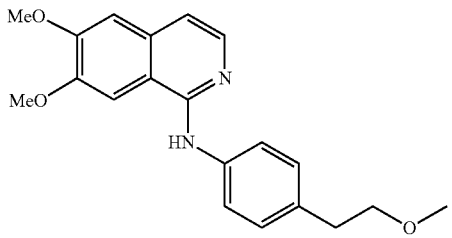
(20)

Compound (20) was prepared according to Scheme 7 as described for (6), starting from (i-c) (0.3 g, 1.34 mmol) and 4-(2-methoxyethyl)aniline (268 mg, 1.6 mmol) to provide (20) (53 mg, yield 11.2%) as white solid. $^1$H NMR (400 MHz, DMSO-d6) δ(ppm) 2.77 (t, J=6.94 Hz, 2H) 3.31 (s, 3H) 3.53 (t, J=6.94 Hz, 2H) 3.88-3.99 (m, 6H) 7.04 (d, J=5.63 Hz, 1H) 7.16 (d, J=8.38 Hz, 2H) 7.22 (s, 1H) 7.66 (d, J=8.38 Hz, 2H) 7.77 (s, 1H) 7.81 (d, J=5.63 Hz, 1H) 8.79 (s, 1H).

Preparation of 6-methoxy-5-methyl-N-(4-(trifluoromethoxy)phenyl)isoquinolin-1-amine (21)

Compound (21) was prepared as detailed in Scheme 10 below.

Scheme 10

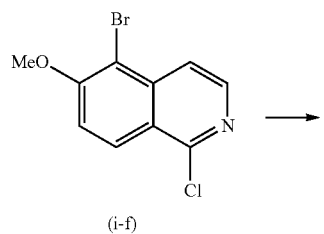
(i-f)

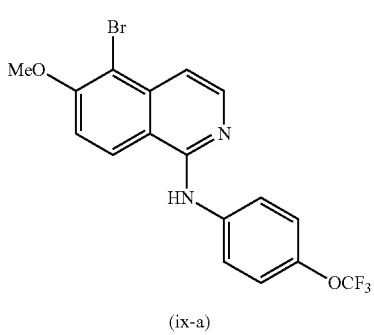
(ix-a)

-continued

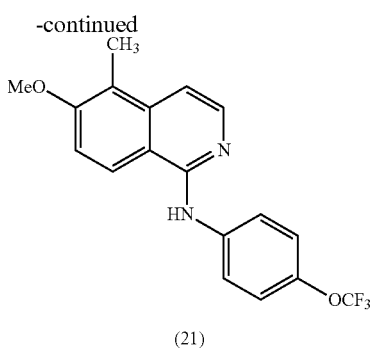
(21)

To a solution of (i-d) (1 g, 5.16 mmol) in ACN (20 mL) was added N-bromosuccinimide (1.01 g, 5.68 mmol) in portions at 20° C. The reaction was stirred at 80° C. for 12 hours. The reaction solution was cooled to 20° C. and filtered. The residue was triturated in ACN (10 mL) and water (10 mL). The solid was collected by filtration and dried in vacuum to give (i-f) (1.15 g, 4.22 mmol, 82% yield) as yellow solid. $^1$H NMR (400 MHz, DMSO-d6) δ(ppm) 8.29-8.38 (m, 2H), 7.91 (d, J=6.00 Hz, 1H), 7.77 (d, J=9.38 Hz, 1H), 4.08 (s, 3H).

Intermediate (ix-a) was prepared according to Scheme 10 as described for (6), starting from (i-f) (50 mg, 183.47 μmol) and 4-(trifluoromethoxy)aniline (64.99 mg, 366.94 μmol) to provide (ix-a) (30 mg, 39.6% yield) as white solid. $^1$H NMR (400 MHz, DMSO-d6) δ(ppm) 9.42 (s, 1H), 8.61 (d, J=9.26 Hz, 1H), 8.05 (d, J=6.00 Hz, 1H), 7.95 (d, J=9.01 Hz, 2H), 7.58 (d, J=9.26 Hz, 1H), 7.32 (br d, J=6.50 Hz, 3H), 4.05 (s, 3H).

Compound (21) was prepared according to Scheme 1-a as following: To a solution of (ix-a) (200 mg, 484.04 μmol) in dioxane (20 mL) was added 2,4,6-trimethyl-1,3,5,2,4,6-trioxatriborinane (364.58 mg, 1.45 mmol, 50% purity, 3 eq) and K$_3$PO$_4$ (205.49 mg, 968.08 μmol) at 20° C. The mixture was degazed with N$_2$ for 2 minutes and Pd(PPh$_3$)$_4$ (55.93 mg, 48.40 μmol, 0.1 eq) was added. The mixture was degazed with N$_2$ for another 2 minutes and the reaction was stirred at 100° C. for 12 hours. The reaction solution was filtered through a pad of celite directly and the filtrate was concentrated under reduced pressure. The residue was purified by column chromatography on silica gel (eluted with ethyl acetate in petroleum ether from 0 to 30%) to give the crude product which was purified again by pre-HPLC and lyophilized to give (21) (79.9 mg, 47% yield) as white solid. $^1$H NMR (400 MHz, DMSO-d6) δ(ppm) 9.25 (s, 1H), 8.43 (d, J=9.38 Hz, 1H), 7.93-8.00 (m, 3H), 7.46 (d, J=9.38 Hz, 1H), 7.30 (d, J=8.38 Hz, 2H), 7.22 (d, J=6.13 Hz, 1H), 3.96 (s, 3H), 2.39 (s, 3H).

Preparation of 6-methoxy-N5,N5-dimethyl-N1-(4-(trifluoromethoxy)phenyl) isoquinoline-1,5-diamine (22)

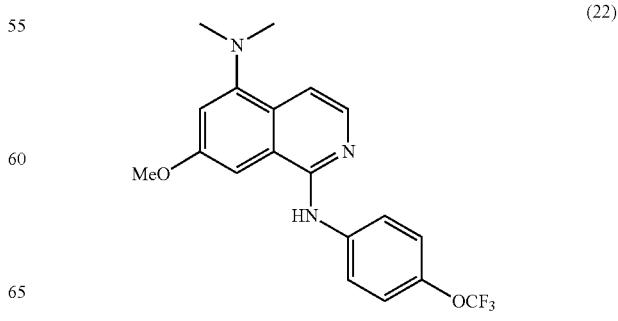
(22)

Compound (22) was prepared according to Scheme 1-a as following: To a solution of (ix-a) (150 mg, 363.03 μmol) in THF (3 mL) was added dimethylamine (2 M, 3.63 mL, 20 eq) and t-BuONa (69.78 mg, 726.06 μmol, 2 eq). Nitrogen was bubbled through the reaction solution for 1 minute, tBuXPhos Pd G3 (28.84 mg, 36.30 μmol, 0.1 eq) was added under nitrogen, and nitrogen was bubbled through the reaction solution for another 1 minute. The reaction was stirred at 80° C. for 12 hours. The reaction mixture was concentrated under reduced pressure. The residue was dissolved in ethyl acetate (10 mL), washed with water (2×2 mL), then brine (2 mL), dried over anhydrous Na$_2$SO$_4$ and filtered. The filtrate was concentrated under reduced pressure. The residue was purified by column chromatography on silica gel (eluted with ethyl acetate in petroleum ether from 0 to 30%) to give the crude product which was purified again by pre-HPLC and lyophilized to give (22) (33.2 mg, 27% yield) as white solid. $^1$H NMR (400 MHz, DMSO-d6) δ(ppm) 9.22 (s, 1H), 8.36 (d, J=9.26 Hz, 1H), 7.96 (d, J=9.26 Hz, 2H), 7.91 (d, J=5.95 Hz, 1H), 7.40-7.53 (m, 2H), 7.30 (d, J=8.82 Hz, 2H), 3.98 (s, 3H), 2.81 (s, 6H).

Preparation of 4-chloro-6-methoxy-N-(4-(trifluoromethoxy)phenyl)isoquinolin-1-amine (23)

Compound (23) was prepared as detailed in Scheme 11 below.

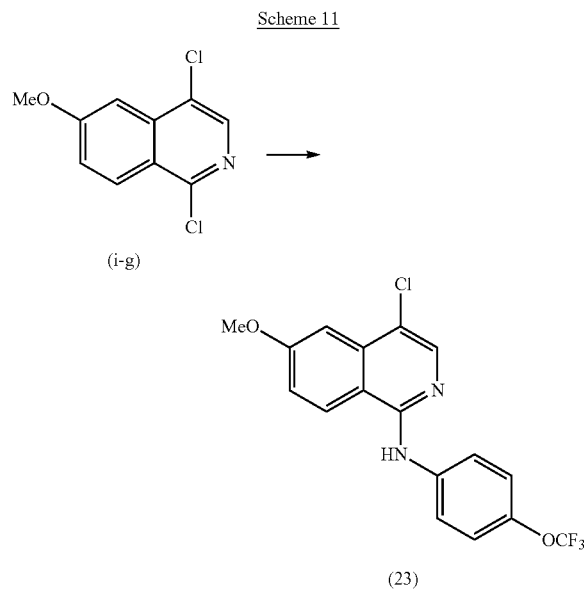

Intermediate (i-g) was prepared as detailed in the Scheme 11-a below:

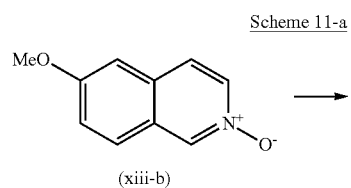

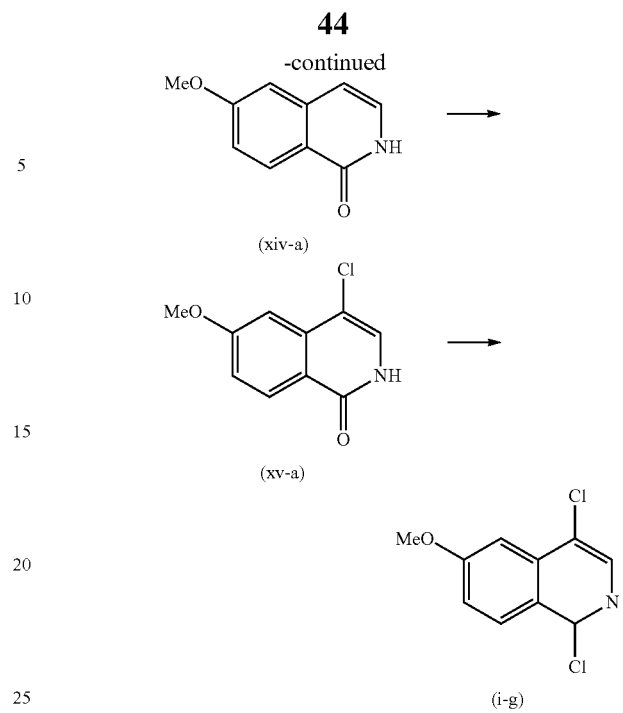

Intermediate (xiii-b) was prepared according to Scheme 7-a as described for (xiii-a), starting from 6-methoxyisoquinoline (10 g, 62.82 mmol) to produce (xiii-b) (11.2 g, 52.92 mmol, 84.2% yield) as light yellow solid. $^1$H NMR (400 MHz, DMSO-d6) δ(ppm) 9.75 (br s, 1H), 8.63 (br d, J=6.88 Hz, 1H), 8.12-8.39 (m, 2H), 7.72 (br s, 1H), 7.60 (br d, J=8.88 Hz, 1H), 4.00 (s, 3H).

To a solution of (xiii-b) (4 g, 18.90 mmol) in DCE (60 mL) was added NaOAc (4.65 g, 56.70 mmol), PyBrOP (17.62 g, 37.80 mmol) and H$_2$O (10 mL) at 20° C. The reaction was stirred at 85° C. for 12 hours. The reaction solution was concentrated under reduced pressure to remove DCE. The residue was poured into water (100 mL) and extracted with DCM (3×50 mL). The combined organic phase was washed with brine (60 mL), dried over anhydrous sodium sulfate and filtered. The filtrate was concentrated under reduced pressure. The residue was purified by column chromatography on silica gel (eluted with ethyl acetate in petroleum ether from 0 to 80%) to give (xiv-a) (2 g, 60.4% yield) as pink solid. $^1$H NMR (400 MHz, DMSO-d6) δ(ppm) 11.05 (br s, 1H), 8.08 (d, J=8.88 Hz, 1H), 7.07-7.17 (m, 2H), 7.04 (dd, J=8.88, 2.50 Hz, 1H), 6.47 (d, J=7.13 Hz, 1H), 3.86 (s, 3H).

To a solution of (xiv-a) (0.95 g, 5.42 mmol) in ACN (20 mL) was added N-chlorosuccinimide (796.53 mg, 5.97 mmol) in portions at 20° C. The reaction was stirred at 80° C. for 4 hours. The reaction solution was cooled to 20° C. and filtered. The residue was washed with ACN (10 mL) and dried in vacuum to give (xv-a) (0.9 g, 4.29 mmol, 79% yield) as pink solid. $^1$H NMR (400 MHz, DMSO-d6) δ(ppm) 11.41 (br s, 1H), 8.16 (d, J=8.88 Hz, 1H), 7.46 (s, 1H), 7.19 (dd, J=8.82, 2.31 Hz, 1H), 7.14 (d, J=2.25 Hz, 1H), 3.92 (s, 3H).

A solution of (xv-a) (0.9 g, 3.66 mmol) in POCl$_3$ (12.65 g, 82.50 mmol, 7.67 mL, 22.56 eq) was stirred at 90° C. for 2 hours. The reaction solution was concentrated under reduced pressure to remove POCl$_3$ and the residue was diluted with ice water (10 mL) and neutralized with 1N NaOH aqueous solution. The solid precipitate was filtered and dried under vacuum to give (i-g) (0.8 g, 96% yield) as a white solid. $^1$H NMR (400 MHz, DMSO-d6) δ(ppm) 8.40

(s, 1H), 8.24 (d, J=9.3 Hz, 1H), 7.53 (dd, J=2.4, 9.3 Hz, 1H), 7.42 (d, J=2.4 Hz, 1H), 4.01 (s, 3H).

Compound (23) was prepared according to Scheme 11 as described for (6), starting from (i-g) (800 mg, 3.51 mmol) and 4-(trifluoromethoxy)aniline (1.24 g, 7.02 mmol, 948.52 μL) to provide (23) 48.8 mg, 48.8% yield) as white solid. ¹H NMR (400 MHz, DMSO-d6) δ(ppm) 9.40 (s, 1H), 8.52 (d, J=9.26 Hz, 1H), 8.06 (s, 1H), 7.90 (d, J=9.13 Hz, 2H), 7.37 (dd, J=9.19, 2.56 Hz, 1H), 7.28-7.35 (m, 3H), 3.97 (s, 3H).

Preparation of 6-methoxy-4-methyl-N-(4-(trifluoromethoxy)phenyl)isoquinolin-1-amine (24)

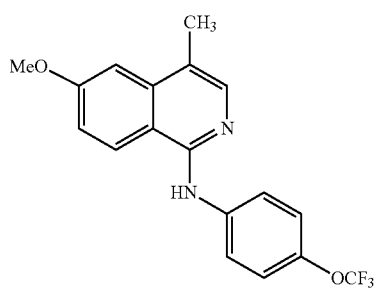 [SMILES: COc1ccc2c(Nc3ccc(OC(F)(F)F)cc3)ncc(C)c2c1]

To a solution of (23) (300 mg, 813.59 μmol) in DMF (6 mL) was added 2,4,6-trimethyl-1,3,5,2,4,6-trioxatriborinane (1.02 g, 4.07 mmol, 1.14 mL, 50% purity), K₂CO₃ (224.89 mg, 1.63 mmol) and tricyclohexylphosphine (45.63 mg, 162.72 μmol, 52.75 μL, 0.2 eq) at 20° C. The mixture was bubbled with N₂ for 2 minutes. Pd(OAc)₂ (18.27 mg, 81.36 μmol, 0.1 eq) was added into the mixture which was bubbled for another 2 minutes. The reaction was stirred at 120° C. for 12 hours. The reaction solution was poured into water (20 mL), extracted with ethyl acetate (3×20 mL), washed with brine (20 mL), dried over sodium sulfate, filtered and the filtrate was concentrated under reduced pressure. The residue was purified by column chromatography on silica gel (eluted with ethyl acetate in petroleum ether from 0 to 30%) to give the crude product which was purified again by pre-HPLC and lyophilized to give (24) (45.8 mg, 16% yield) as white solid. ¹H NMR (400 MHz, DMSO-d6) δ(ppm) 9.14 (s, 1H), 8.45 (d, J=9.17 Hz, 1H), 7.93 (d, J=9.05 Hz, 2H), 7.82 (d, J=0.61 Hz, 1H), 7.22-7.34 (m, 3H), 7.17 (d, J=2.57 Hz, 1H), 3.95 (s, 3H), 2.42 (s, 3H).

Preparation of 4-bromo-6-methoxy-N-(4-(trifluoromethoxy)phenyl)isoquinolin-1-amine (25)

Compound (24) was prepared as detailed in Scheme 12 below.

Scheme 12

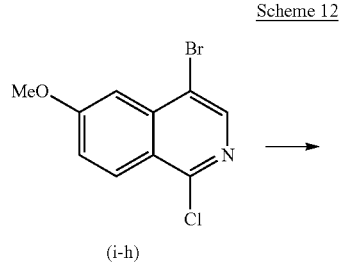

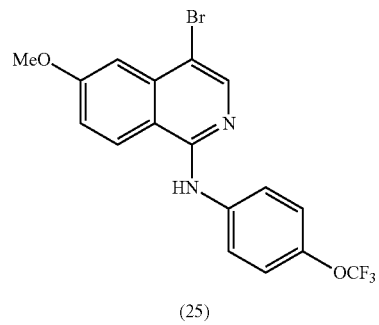

Intermediate (i-h) was prepared according to Scheme 11-a as described for (i-g), starting from (xiv-a) (1 g, 5.71 mmol) and N-bromosuccinimide (1.12 g, 6.28 mmol) to provide in two steps intermediate (i-h) 920 mg, 3.38 mmol, 85.8% yield) as white solid. ¹H NMR (400 MHz, DMSO-d6) δ(ppm) 8.52 (s, 1H), 8.25 (d, J=9.26 Hz, 1H), 7.54 (dd, J=9.26, 2.43 Hz, 1H), 7.40 (d, J=2.43 Hz, 1H), 4.02 (s, 3H).

Compound (25) was prepared according to Scheme 12, following the same procedure described for (6), starting from (i-h) (200 mg, 733.88 μmol) and 4-(trifluoromethoxy)aniline (259.97 mg, 1.47 mmol) to provide (25) (30.5 mg, 10% yield) as white solid. ¹H NMR (400 MHz, DMSO-d6) δ(ppm) 9.41 (s, 1H), 8.51 (d, J=9.29 Hz, 1H), 8.16 (s, 1H), 7.83-7.96 (m, 2H), 7.24-7.42 (m, 4H), 3.97 (s, 3H).

Preparation of 6-methoxy-4-methyl-N-(4-(trifluoromethoxy)phenyl)isoquinolin-1-amine (26)

Compound (26) was prepared as detailed in Scheme 13 below.

Scheme 13

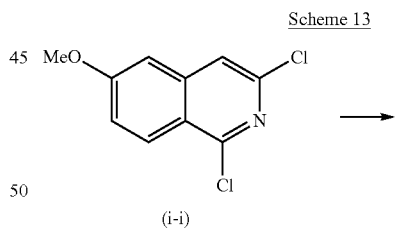

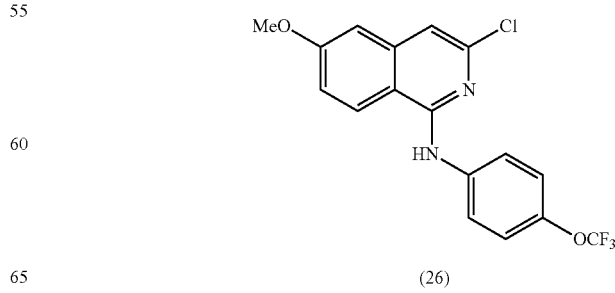

Intermediate (i-i) was prepared as detailed in the Scheme 13-a below:

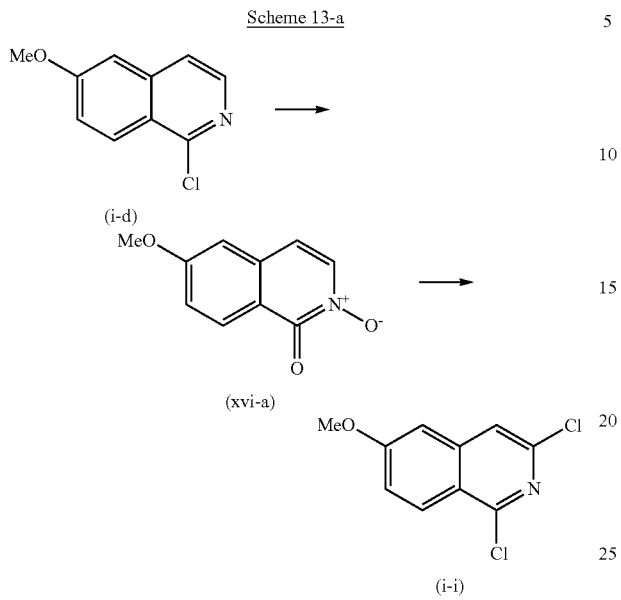

Scheme 13-a (i-d)

(xvi-a)

(i-i)

Intermediate (xvi-a) was prepared according to Scheme 7-a as described for (xiii-a), starting from Intermediate (i-d) (1 g, 5.16 mmol) to provide (xvi-a) (0.55 g, 43% yield) as a white solid. $^1$H NMR (400MHz, DMSO-d6) δ(ppm) 9.79 (d, J=1.9 Hz, 1H), 8.64 (dd, J=2.0, 7.1 Hz, 1H), 8.37-8.23 (m, 2H), 7.71 (d, J=2.4 Hz, 1H), 7.59 (dd, J=2.5, 9.1 Hz, 1H), 3.99 (s, 3H).

Intermediate (i-i) was prepared according to Scheme 13-a as described for (i-c), starting form (xvi-a) (0.55 g, 2.23 mmol) to provide (i-i) (0.42 g, 82.4% yield) as white solid. $^1$H NMR (400 MHz, DMSO-d6) δ(ppm) 8.16 (d, J=9.2 Hz, 1H), 7.96 (s, 1H), 7.48-7.37 (m, 2H), 3.94 (s, 3H).

Compound (26) was prepared according to Scheme 13 as described for (6), starting from (i-i) (0.27 g, 1.02 mmol) and 4-(trifluoromethoxy)aniline (198.86 mg, 1.12 mmol) to provide (26) (40.9 mg, 10.4% yield,) as white solid. $^1$H NMR (400 MHz, DMSO-d6) δ(ppm) 9.50 (s, 1H), 8.45 (d, J=9.9 Hz, 1H), 8.03-7.81 (m, 2H), 7.35 (br d, J=8.4 Hz, 2H), 7.30-7.15 (m, 3H), 3.90 (s, 3H).

Preparation of N$^6$,N$^6$-dimethyl-N$^1$-(4-(trifluoromethoxy)phenyl)isoquinoline-1,6-diamine (27)

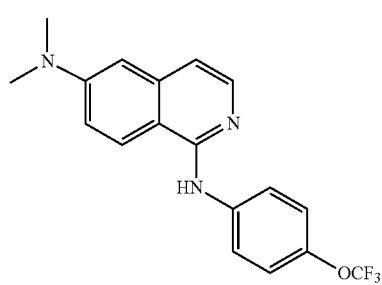

(27)

To a mixture of (13) (100 mg, 295.2 μmol, 1 eq), t-BuXPhos (12.5 mg, 29.52 μmol, 0.1 eq), NaOtBu (56.75 mg, 590.4 μmol, 2 eq) and tBuXPhos Pd G3 (23.4 mg, 29.52 μmol, 0.1 eq) in THF (1 mL) was added dimethylamine (2 M in tetrahydrofuran, 2.9 mL, 20 eq). The mixture was stirred at 100° C. for 36 hours under N$_2$ atmosphere. The mixture was filtered and the filtrate was concentrated to give a crude product which was then purified by column chromatography eluted with petroleum ether/ethyl acetate (100:1 to 1:1) to give Example (27) (138.7 mg, 399.3 μmol, 33.8% yield) as a white solid. $^1$H NMR (400MHz, DMSO-d6) δ (ppm) 9.08 (s, 1H), 8.31 (d, J=9.4 Hz, 1H), 8.08-7.87 (m, 2H), 7.80 (d, J=5.8 Hz, 1H), 7.28 (d, J=8.5 Hz, 2H), 7.20 (dd, J=2.6, 9.3 Hz, 1H), 6.98 (d, J=5.9 Hz, 1H), 6.79 (d, J=2.5 Hz, 1H), 3.06 (s, 6H).

Preparation of 1-((4-(trifluoromethoxy)phenyl)amino)isoquinoline-6-carbonitrile (28)

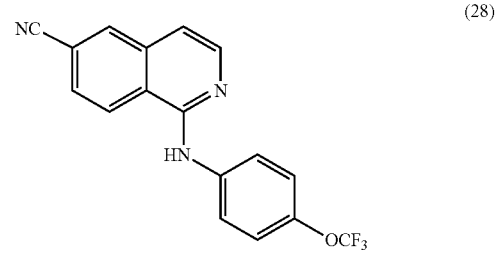 [SMILES: N#Cc1ccc2c(Nc3ccc(OC(F)(F)F)cc3)nccc2c1]

(28)

A mixture of (13) (0.6 g, 1.77 mmol, 1 eq), Zn(CN)$_2$ (624.0 mg, 5.3 mmol, 337.3 uL), PdCl$_2$ (dppf) (129.6 mg, 177.14 μmol, 0.1 eq) in DMF (36 mL) was stirred at 150° C. for 12 hours under nitrogen. The reaction mixture was poured into cold water (50 mL) and extracted with ethyl acetate (3×50 mL). The organic phases were combined, washed with water (2×30 mL), brine (2×30 mL), dried over Na$_2$SO$_4$, filtered and the filtrate was concentrated under reduced pressure to give a residue which was then purified by prep-TLC to give (28) (130 mg, 394.8 μmol, 22.2% yield) as a yellow solid. $^1$H NMR (400 MHz, DMSO-d$_6$) δ (ppm) 9.54 (s, 1H), 8.70 (d, J=8.8 Hz, 1H), 8.48 (d, J=1.0 Hz, 1H), 8.14 (d, J=5.8 Hz, 1H), 8.01-7.91 (m, 3H), 7.38-7.22 (m, 3H).

Preparation of methyl 1-((4-(trifluoromethoxy)phenyl)amino)isoquinoline-6-carboxylate (29)

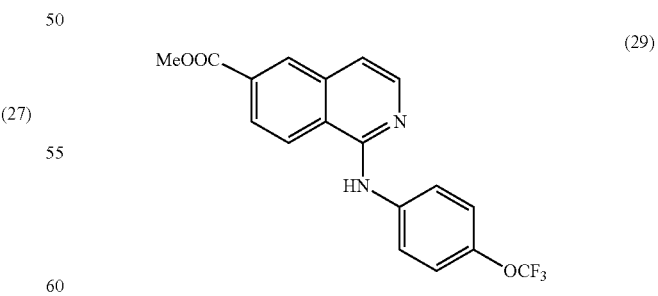

(29)

A mixture of Example (28) (1 g, 3.04 mmol, 1 eq) and HCl/Methanol (4 M, 100 mL) was stirred at 65° C. for 24 hours. The reaction mixture was concentrated to give a residue, which was poured into aqueous NaHCO$_3$ (100 mL) and extracted with ethyl acetate (3×50 mL). The organic phases were combined, washed with brine (50 mL), dried over Na$_2$SO$_4$, filtered and the filtrate was concentrated under reduced pressure to give a crude product. The crude was purified by column chromatography on silica gel eluted with petroleum ether/ethyl acetate (100:1 to 1:1) to give a product which was then further triturated with petroleum/ ethyl acetate (4:1, 20 mL) to give Example (29) (250.5 mg, 667.2 μmol, 22% yield) as a yellow solid. $^1$H NMR (400 MHz, DMSO-d6) δ(ppm) 9.50 (s, 1H), 8.65 (d, J=8.8 Hz, 1H), 8.51 (s, 1H), 8.16-8.05 (m, 2H), 7.99 (d, J=9.0 Hz, 2H), 7.42 (d, J=5.8 Hz, 1H), 7.34 (br d, J=8.8 Hz, 2H), 3.95 (s, 3H).

Preparation of 6-ethyl-N-(4-(trifluoromethoxy)phenyl)isoquinolin-1-amine (30)

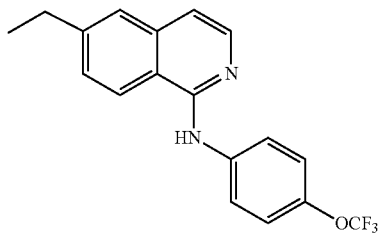 [SMILES: CCc1ccc2c(Nc3ccc(OC(F)(F)F)cc3)nccc2c1]

To a solution of (13) (300 mg, 885.71 μmol) in dioxane (2.4 mL) and water (0.6 mL) was added 4,4,5,5-tetramethyl-2-vinyl-1,3,2-dioxaborolane (136.41 mg, 885.71 μmol, 1 eq), K$_3$PO$_4$ (752.02 mg, 3.54 mmol), Pd(OAc)$_2$ (39.77 mg, 177.14 μmol, 0.2 eq) and Bu$_3$PHBF$_4$ (51.39 mg, 177.14 μmol, 0.2 eq) at 20° C. under N$_2$ atmosphere. The mixture was stirred at 100° C. for 12 hours under N$_2$. The reaction mixture was filtered and the filtrate was concentrated under reduced pressure to give a crude product. The crude product was purified by prep-TLC to give N-(4-(trifluoromethoxy)phenyl)-6-vinylisoquinolin-1-amine (150 mg, 454.13 μmol, 51% yield) as a white solid.

To a solution of N-(4-(trifluoromethoxy)phenyl)-6-vinylisoquinolin-1-amine (150 mg, 454.13 μmol) in EtOH (2 mL) was added Pd/C (50 mg, 36.76 μmol, 10% purity). The suspension was degassed under vacuum and purged with H$_2$ several times. The mixture was stirred under H$_2$ (122.0 ug, 60.5 μmol) (15 psi) at 20° C. for 12 hours. The suspension was filtered through a pad of celite and the filter cake was washed with EtOH (3×3 mL). The filtrate was concentrated to dryness to give the crude product. The crude product was purified by prep-HPLC. The elution was adjusted with aqueous NaHCO$_3$ to pH~7 and then extracted with ethyl acetate (3×20 mL). The organic layer was dried with Na$_2$SO$_4$, filtered and concentrated under reduced pressure to give (30) (55.5 mg, 167.01 μmol, 37% yield) as a yellow solid. $^1$H NMR (400 MHz, CHLOROFORM-d) δ(ppm) 8.05 (br d, J=6.0 Hz, 1H), 7.84 (br d, J=8.6 Hz, 1H), 7.75-7.65 (m, 2H), 7.57 (s, 1H), 7.43 (br d, J=8.8 Hz, 1H), 7.23 (br d, J=8.5 Hz, 2H), 7.13 (br d, J=5.8 Hz, 1H), 2.85 (q, J=7.6 Hz, 2H), 1.35 (t, J=7.6 Hz, 3H).

Example 2: In Vitro Effects of Compounds of the Invention in Enhancing Glucose Uptake and Lactate Levels Secretion To assess for the effect of the compounds of the invention, those were tested in primary astrocytes, as well as a cellular model of GLUT1-DS, i.e. primary astrocytes that exhibit GLUT1 down regulation, as described below. Secretion of lactate was measured indirectly through the acidification of extracellular medium using extracellular pH sensor SNARE-5F-(AND-6)-CAR (SNARF5) as described below.

Extracellular Medium Acidification (SNARF5)

Secretion of lactate was measured indirectly through the acidification of extracellular medium using extracellular pH sensor SNARE-5F-(AND-6)-CAR (SNARF5). After washing cells twice with stimulation medium (DMEM (D5030, Sigma), 1 mM NaHCO$_2$, and 5 mM Glucose, pH 7.4) at 37° C., cells were stimulated with compounds at a final concentration ranging from 10 nM to 30 μM in 50 μl per well of stimulation medium supplemented with 10 μM of SNARF5 (Life Technologies Corporation). Each compound was tested in two different plates for duplicates. After 90 min stimulation, fluorescence was read at exc. (excitation) 480 nm/emm. (emission) 580 nm and at exc 480 nm/emm. 630 nm. The ratio of fluorescence between 630 nm and 580 emission values, which is proportional to extracellular pH, was calculated. In each plate, 8 wells were used for negative controls (DMSO 0.1%) and 8 wells were used for positive controls (CCCP 2 μM in DMSO).

Table 3 below lists compounds that are active on the extracellular medium acidification (SNARF5) assay in astrocytes in vitro, which indicates their ability to produce lactate. '+' indicates activity of compounds with EC50>5 μM; '++' indicates activity of compounds with EC50<5 μM.

TABLE 3

| Example | Activity |
|---------|----------|
| 1 | + |
| 2 | + |
| 3 | + |
| 4 | + |
| 5 | + |
| 6 | + |
| 7 | + |
| 8 | + |
| 9 | + |
| 10 | + |
| 11 | ++ |
| 12 | + |
| 13 | + |
| 14 | + |
| 15 | + |
| 16 | ++ |
| 17 | + |
| 18 | + |
| 19 | ++ |
| 20 | ++ |
| 21 | ++ |
| 22 | ++ |
| 24 | + |
| 25 | + |
| 26 | + |
| 27 | ++ |
| 29 | ++ |
| 30 | ++ |

Cell Cultures

Primary cultures of cerebrocortical astrocytes were obtained from 1 to 2-day-old OF1 mouse pups (Charles River). Briefly, cortices were isolated and minced in small pieces under a dissecting microscope. The cells were incubated for 30 min at 37° C. in a solution containing 20 U/ml papain, 1 mM L-cysteine and 10 kU/ml DNase I. After dissociation, papain activity was stopped by the addition of fetal calf serum (FCS). Single-cell suspension was then obtained by mechanical dissociation, which consisted in cells trituration in a DMEM D7777 medium supplemented with 44 mm NaHCO3, 10 ml/L antibiotic/antimycotic solution and 10% FCS. The cells were seeded at an average density of ~10'000 cells/cm$^2$ on poly-D-lysine coated 96- or 12-well culture plates, depending on their use, and grown in DMEM D7777 medium supplemented with 44 mm NaHCO3, 10 ml/L antibiotic/antimycotic solution and 10% FCS at 37° C. in a humidified atmosphere containing 5% CO2/95% air. Culture medium was renewed twice a week. Cells were stimulated and harvested between DIV14 and DIV17, when confluence and cell growth were optimal.

Extracellular Lactate Quantification

Secretion of L-lactate was measured in the extracellular medium of 96-well plated astrocytes after 90 min stimulation (at 37° C., in 5% CO2/95% air conditions) with Vehicle (DMSO), the compounds of the invention (100 nM to 100 µM) or positive control. The positive control consisted in carbonyl cyanide m-chlorophenyl hydrazine (CCCP, 2 µM), an inhibitor of mitochondrial oxidative phosphorylation that hence leads to enhanced glycolysis and secretion of lactate. Stimulation medium was composed of D5030 medium complemented with 5 mM D-glucose and 44 mM sodium bicarbonate, pH 7.2. To quantify lactate concentrations in the extracellular medium, 200 µl of a 0.2M Glycine-semicarbazide buffer (pH 10) containing 3 mM NAD and 14 U/ml LDH was added to each well of a 96-well plate containing 30 µl aliquots of extracellular medium. Samples were incubated at 37° C. for 1 h. Fluorescence intensity (340 nm excitation/450 nm emission), which represents the amount of NADH produced, was measured, and lactate concentration values were determined relative to a standard curve of L-lactate concentrations.

The release of lactate from primary mouse astrocytes treated with compound (1) at 10 µM was quantified by (FIG. 1). Accumulation of lactate in the extracellular medium was measured over a period of 1.5 h. Compounds (1) to (4) were tested at different concentrations ranging from 1 nM to 100 µM to determine their EC50 and minimal effective concentrations and compound (1) has an EC50 of 7.023 µM, while an effect already significant at concentrations below 1 µM could be monitored. Compounds (2) to (4) had effects on astrocyte-mediated lactate secretion of similar ranges, with EC50 of 10.1 µM (2), 10.5 µM (4) and 10.9 µM (3). Maximal effects of the compounds were 38.6% (1), 38% (2), 31% (4) and 76% (3) when compared to the effect of the positive control (100%) for compounds (1) to (4), respectively.

Intracellular Glycogen Quantification

Astrocytes grown on 12-well plates were used for intracellular glycogen quantifications. Cells were stimulated with Vehicle (DMSO), with compounds of the invention (10 µM), or with a positive control for 180 min, at 37° C. 5% CO2/95% air in D5030 medium complemented with 5 mM D-glucose and 44 mM sodium bicarbonate (pH 7.2). Positive control consisted in an activator of glycogen phosphorylase, which hence triggers glycogen degradation in astrocytes (10 µM). At the end of the stimulation, medium was removed and replaced with 600 µl of 30 mM Tris HCl, and stored at −20° C.

First, the amount of proteins in each sample was quantified to assess whether harvested astrocytes from primary cell cultures yielded enough and equivalent amounts of proteins on each replicates. Proteins were quantified using the micro BCA Protein Assay kit (Thermo Scientific), according to manufacturer's instructions. Next, intracellular glycogen concentrations were quantified using a 250 µl-aliquot of the same stimulated, thawed, and sonicated cell lysate. After an incubation period of 30 min at 90° C. and 400 rpm, 28 µl of a 0.1M acetic acid/sodium acetate buffer (pH 4.6) was added to each lysate aliquots, which were then separated in two. Each split aliquots received either 5 µl of amyloglucosidase or H2O, and incubated for 120 min at 37° C. After centrifugation at 16'000 G for 5 min, 20 µl of supernatant were placed in a 96-well plate, to which 150 µl of a mix containing 0.67 mM ATP, 0.67 mM NADP, 1.8% hexokinase/ glucose-6-phosphate dehydrogenase in a 0.1M Tris Buffer-HCl/3.3 mM magnesium (pH 8.1) buffer was added. Fluorescence intensity (340 nm excitation/440 nm emission) was measured using a Safire 2 spectrophotometer. Glucose concentrations were assessed relative to a glucose standard curve, and glycogen concentrations were calculated by subtracting glucose values of samples that had received amyloglucosidase (i.e. that had degraded their glycogen stores) to samples that had not.

Figure 2:
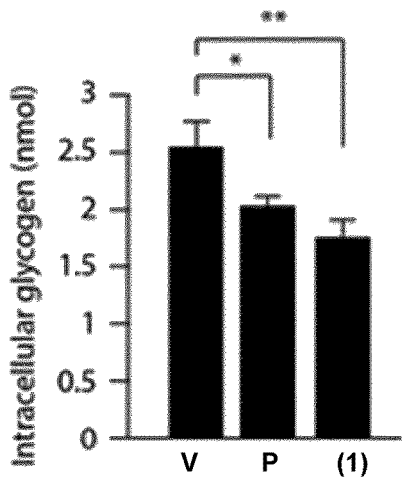
FIG. 2 represents intracellular levels of glycogen in astrocytes 3 hours after stimulation with Compound (1) (10 µM) as described in Example 2, compared to that of Vehicle alone (V) or a positive control known stimulate degradation of glycogen through the activation of glycogen phosphorylase (P; 10 µM), represented as the mean of intracellular glycogen levels (nmoles)±SEM; n=6; *p<0.05; **p<0.01.

Intracellular levels of glycogen, which is the main source of glucose storage in the brain, were analyzed in primary astrocytes after treatment with compound (1) (10 µM, 3 h) (FIG. 2) and it was observed that compound (1) significantly enhances the degradation of intracellular glycogen, which may act, at least in part, as the energy fuel necessary to produce lactate by astrocytes during the process of aerobic glycolysis.

MTT Mitochondrial Activity Assay

To monitor mitochondrial activity in astrocytes, which is linked to the metabolic process of glycolysis and production of lactate, astrocytes in 96-well plates were stimulated for 24 h (37° C. 5% CO2/95% air) with the compounds of the invention ranging from 0.2 to 200 µM.

After stimulation, 5 mg/ml thiazol blue tetrazolium bromide (MTT) in D5030 medium complemented with 5 mM D-glucose and 44 mM sodium bicarbonate (pH 7.2) was added to each well, and cells were incubated for 4 h at 37° C. (5% CO2). The medium was then removed and the amount of reduced MTT, i.e. formazan, solubilized in DMSO (50 µl/well) was determined using a spectrophotometer (absorbance of 570 nm).

Figure 3:
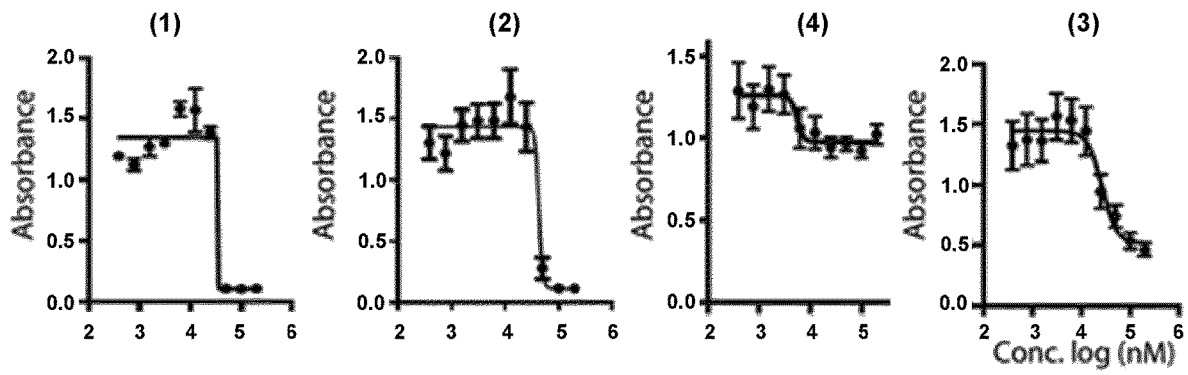
FIG. 3 shows in vitro mitochondrial activity of primary astrocytes measured as described in Example 2 at 24 hours after treatment with compounds (1) to (4) of the invention at concentrations ranging from 100 nM to 200 µM, represented as mean absorbance of MTT colorimetric assay±SEM; n=9.

The mitochondrial activity in primary astrocytes treated with Compounds (1) to (4) at concentrations ranging from 1 nM to 200 µM. After 24 h, mitochondrial activity was monitored in MTT colorimetric assay as described above (FIG. 3). IC50 were 34.4 µM (1), 42.9 µM (2), 5.5 µM (4) and 26.6 µM (3). Remaining mitochondrial activity at maximum concentrations of the compounds were 8.05% (1), 7.86% (2), 77.3% (4) and 35.9% (3) compared to vehicle respectively.

Altogeter, those data support that compounds of the invention stimulate lactate secretion and glycogenolysis by astrocytes in vitro.

2-deoxyglucose (2DG) Uptake

Astrocytes grown on 12-well plates and transfected with either scramble siRNA or GLUT1 siRNA were used. 1 day after having replaced transfection medium (DIV13), 2DG uptake was measured after treatment for 30 min with Vehicle (0.1% DMSO) or with the compound of the invention (1) (concentrations of 1 or 10 µM). During treatment, 1 mM 2DG was added to the medium for assessment of 2DG uptake. At the end of the stimulation, medium was removed and replaced with 150 µl NaOH 0.1M, and stored at −20° C. After thawing, cells were collected using cell scraper and heated for 40 min at 85° C. Then, 150 ul HCl 0.1M and TAE buffer 200 mM was added to each condition. 20 µl were added to a transparent 96-well plate and 2DG was quantified by addition of a reaction solution containing 50 mM TAE, 50 mM KCl, 0.02% BSA, 0.1 mM NADP, 0.2 U/ml diaphorase, 2 mM resazurin and 20 U/ml glucose-6-phosphate dehydrogenase. Concentration of 2DG in samples were calculated by comparison with standard curve of deoxy-glucose-6-phosphate ranging from 0 to 1 nmoles.

siRNA-Mediated GLUT1 Downregulation

After 10 days in vitro (DIV), primary astrocytes grown in 12-well plates were transfected as following: culture medium was removed and replaced with transfection medium that consisted in 1.5 ml of DMEM D5030 (per well of 12-well plate) supplemented with 44 mM NaHCO$_3$ and 5 mM D-Glucose, in addition to 2 μl Lipofectamine 2000, 40 μl Opti-MEM and 40 μM scramble siRNA (siRNA that did not match any known mRNA sequence) or GLUT1-siRNA (siRNA that matched GLUT1 mRNA sequence). Scramble and GLUT1 siRNA sequences were as following:

```
Scramble siRNA:
                                      (SEQ ID NO.: 1)
AGGUAGUGUAAUCGCCUUG
and GLUT1 siRNA:
                                      (SEQ ID NO.: 2)
GUAUAGAUGGAAGAUAUUU.
```

Cells were grown in transfection medium for 3 days at 37° C. in a humidified atmosphere containing 5% $CO_2$/95% air. After 3 days, transfection medium was replaced with DMEM D5030 supplemented with 44 mM NaHCO$_3$ and 5 mM D-Glucose (1 ml per well).

Figure 4:
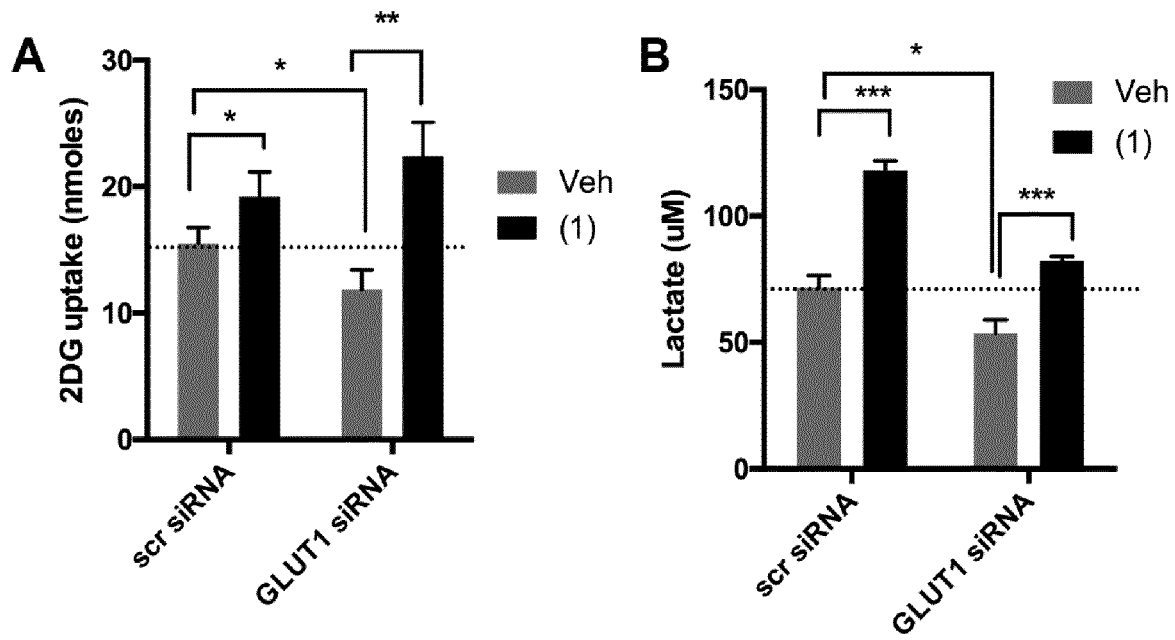
FIG. 4 shows the metabolic effect of compound of the invention (1) in a cellular model of GLUT1-DS, i.e. primary astrocytes that exhibit GLUT1 downregulation. A: decreased 2DG uptake by astrocytes transfected with GLUT1 siRNA compared to scramble siRNA (scr siRNA), which was restored after treatment with compound of the invention (1), represented as mean +SEM of 2DG uptake (pmoles); n=6. B: decreased lactate secretion by astrocytes transfected with GLUT1 siRNA compared to scramble siRNA, which was restored after treatment with compound of the invention (1), represented as mean +SEM of extracellular lactate (µM); n=6.

2DG uptake after treatment with Veh or compound of the invention (1) was measured in astrocytes transfected with scramble siRNA or GLUT1 siRNA (FIG. 4A). Results indicate that the reduction of GLUT1 mRNA expression in GLUT1 siRNA-transfected astrocytes leads to a significant reduction of 2DG uptake, while treatment with compound (1) significantly enhances 2DG uptake in astrocytes transfected with scramble siRNA and with GLUT1 siRNA.

Lactate secretion after treatment with Veh or compound of the invention (1) was measured in astrocytes transfected with scramble siRNA or GLUT1 siRNA (FIG. 4B). Results indicate that the reduction of GLUT1 mRNA expression in GLUT1 siRNA-transfected astrocytes leads to a significant reduction of lactate secretion, while treatment with compound (1) significantly enhances lactate secretion by astrocytes transfected with scramble siRNA and with GLUT1 siRNA.

Example 3: In Vivo Effects of Compounds of the Invention

To assess for the effect of the compounds of the invention on brain extracellular levels of lactate, they have been tested though the in vivo monitoring of lactate levels after treatment with the compounds of the invention as follows. Further, to assess for the effect of the compounds of the invention in neurodegenerative disorder, since production of lactate in the brain is considered as being a key element underlying neuroprotection in neurodegenerative disease, including ALS (Lee et al., 2012, supra; Finstenvald et al., 2015, *Curr. Drug Targets*, 21(25):3570-81), they have been tested though in a mouse model of ALS as follows. Finally, in order to document the role of compounds of the invention on long-term memory, knowing that the production of lactate is a key element underlying synaptic plasticity and memory consolidation (Suzuki et al, 2011, supra; Yang et al., 2014, supra; Tadi et al., 2015, supra), they have been tested in an inhibitory avoidance (IA) test as described below.

All experiments were carried out in strict accordance with the Swiss Federal Guidelines for Animal Experimentation and were approved by the Cantonal Veterinary Office for Animal Experimentation (Canton of Vaud or Canton of Geneva, Switzerland).

For pharmacodynamics (FIG. 5) and cognition (FIG. 7) experiments, adult male C57Bl/6J wild-type mice weighting 18-28 g (8 weeks of age) were used (Charles River). For ALS mouse models (FIG. 6), G93A SOD1 transgenic male and female mice on B6.SJL1-Gur/J background were used (Jackson Laboratory).

Animals were housed in groups of 3-5 in polypropylene cages (30×40×15 cm) with wire mesh top in a temperature (22±2° C.) and humidity (55±15%) controlled environment on a 12 hour light cycle (07.00-19.00 h lights on), except after surgeries when animal were housed individually. The samples (Vehicle or compounds of the invention) were administered per os (gavage) in a solution made of water supplemented with 0.4% hydroxypropyl methylcellulose (HPMC) Methocel 4KM (w/v) and 0.25% Tween-20 (v/v), as previously described (Thackaberry et al., 2010, Toxicol Sci., 117(2):485-92). Concentrations of the compounds tested ranged from 10 to 100 mg/kg.

In Vivo Pharmacodynamics—Lactate Biosensors

Figure 5:
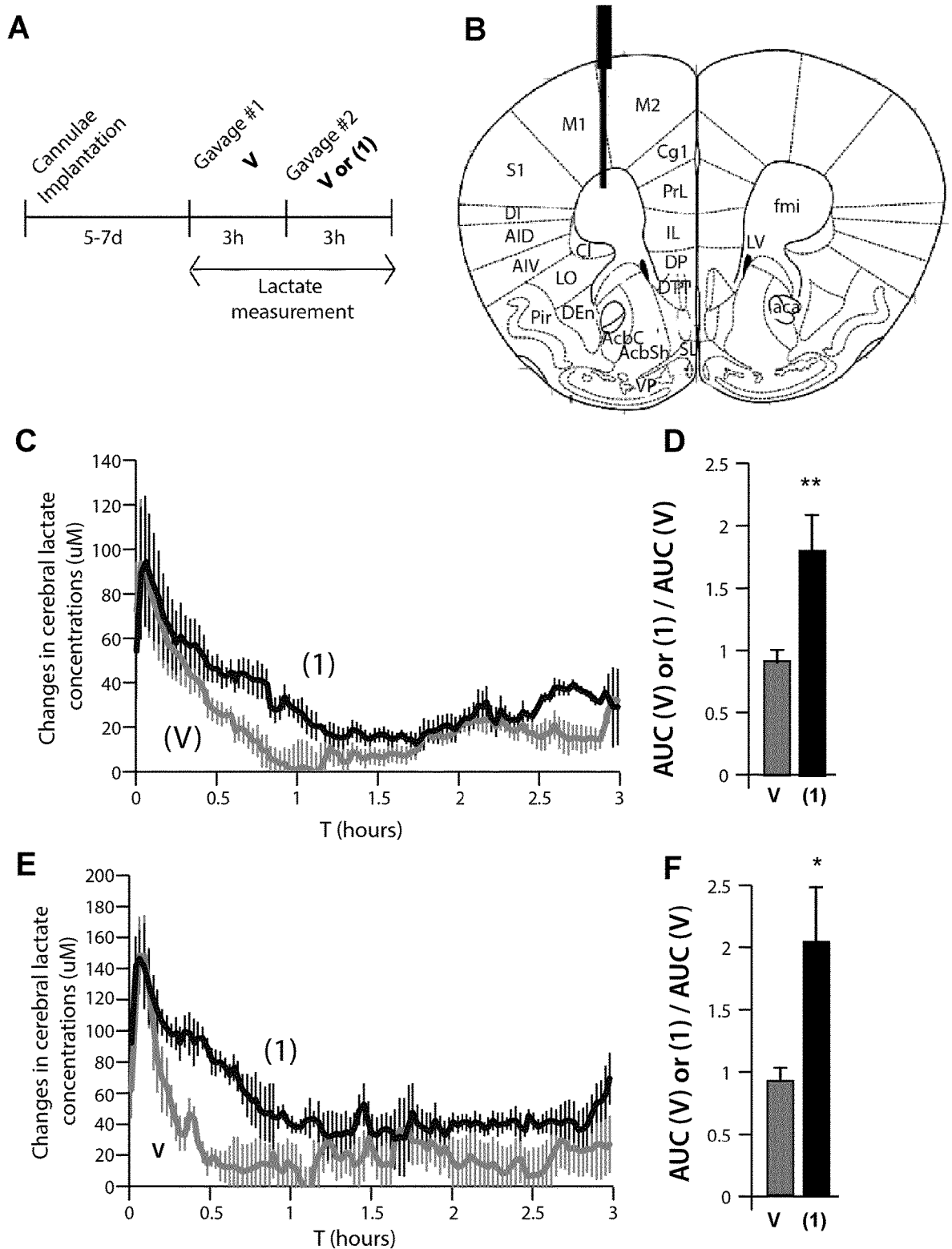
FIG. 5 shows the monitoring of cerebral lactate production as described in Example 2. A: experimental schedule with surgical implantation of cerebral cannulae 5 to 7 days prior administration of Vehicle (V) followed, 3 h later by administration of (V) or compound invention (1) of the invention for another 3 hours (10 mg/kg or 100 mg/kg); B: Localization of the lactate probe implanted in mouse brain; C,E: Fluctuations of intracerebral lactate levels versus time (T) recording after administration of (V), followed 3 h later by (V), (1) at 10 mg/kg (C) or (1) at 100 mg/kg (E); D,F: Area under curve (AUC) calculated from lactate fluctuations shown in (C) and (D). Ratio of AUC after $2^{nd}$ gavage with (V) or (1) at 10 mg/kg (D), as well as (V) or (1) at 100 mg/kg (F) over AUC after $1^{st}$ gavage with V, which serves as internal control. Data are expressed as the mean AUC ratio±SEM; n=7; *p<0.05; **p<0.01.
Figure 6:
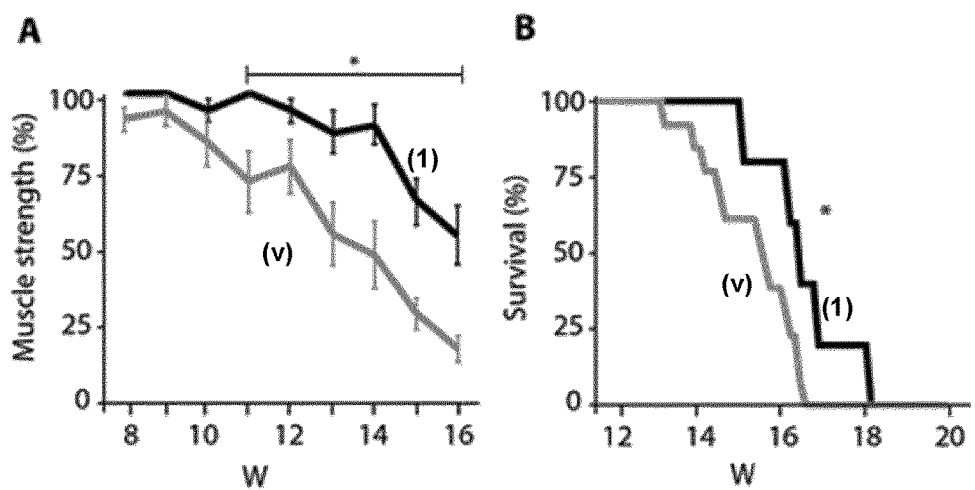
FIG. 6 shows the neuroprotective effect of compound of the invention (1) in the G93A SOD1 mouse model of ALS as described in Example 2. A: Grip strength test of G93A SOD1 male mice treated with Vehicle (V) or compound (1) (10 mg/kg) from postnatal day 30 to final stage (paralysis) measured by evolution of muscle strength every week (W) in the grip test procedure. Results are shown as percentage of maximal grip time, i.e. 5 minutes. Data are expressed as the average of the muscle strength percentage±SEM; n=6; *p<0.05; B: Survival percentage (%) of mice in weeks (W) treated from postnatal day 30 (weaning) to final stage (paralysis) with Vehicle alone or (1) (10 mg/kg) as measured with Kaplan-Meier curves; n=6; *p<0.05.

Cerebral extracellular levels of lactate were monitored in vivo using lactate biosensors (Pinnacle Technology), according to the manufacturer's instructions. Cannulae were surgically implanted in the cerebral motor cortex areas M1/M2 (coordinates: +1.94 mm (to bregma), lateral −1.4 mm (to mideline), ventral −1.0mm (to dura)) of isoflurane-anesthetized mice 5 to 7 days prior experiment. After surgery, mice were monitored closely and received analgesic treatment for at least 4 days. After mice had fully recovered from surgery, compounds of the invention of vehicle were administered per os as previously described and cerebral levels of extracellular lactate were dynamically recorded for 6 hours using lactate biosensors. Mice were administered vehicle alone first, followed 3 hours later by vehicle or Compound (1) (10 or 100 mg/kg). Concentrations of cerebral extracellular lactate were calculated from lactate probe electric signals using post-calibration values. Each signal of lactate fluctuation after compound (or vehicle) administration was expressed as a fold change relative to the lactate fluctuation following the first administration of vehicle alone, each animal hence being its own control. Area Under the Curve (AUC) of lactate concentration curves were calculated using Graphpad Prism and the ratio of AUC after drug over Vehicle administration was calculated. Extracellular concentrations of L-lactate were measured in real time in freely moving animals for 3 hours after administration of Vehicle or Compound (1) (FIG. 5). Results indicate that treatment with Compound (1) at 10 mg/kg and 100 mg/kg significantly increases extracellular lactate levels in the brain of treated mice, as compared to vehicle (FIG. 5 C-F).

SOD1 G93A Mouse ALS Model

Transgenic mice on B6.SJL1-Gur/J background overexpressing the human mutated gene G93A SOD1 were used. Mating colonies were composed of wild-type female mice and SOD1 G93A male mice, both on B6. SJL1-Gur/J background (purchased from Jackson Laboratory). F1 pups were genotyped after ear punching at weaning, using quantitative PCR (qPCR), which allowed determining the number of SOD1 copies in each mouse. To test for the potential therapeutic effect of the administered compound, SOD1 mice were given orally the compound of the invention (10 mg/kg) or vehicle every day from post-natal day 30 (weaning) throughout their entire life. 3 groups were compared: wild-type mice treated with Vehicle, G93A SOD1 mice treated with Vehicle and G93A SOD1 mice treated with the compound of the invention. Each mouse's weight was recorded every day throughout the entire treatment, while neuromuscular function was measured once a week. Evaluation of neuromuscular function consisted in testing muscle strength using the grip test described below.

Grip Test

The experiment was conducted in a room with a low light intensity (30 lux) to reduce stressful environment. Mice were individually placed upside-down on the centre of a 35 cm-high 42×42 cm grid, which was placed on a bubble pack-lined table, for a maximal period of 5 min. Mice ability to grip the grid (time [s]) was measured in order to assess for their muscle strength and coordination. Each mouse was tested on 3 consecutive trials with at least 20 min intervals between trials, and maximal value among the 3 trials was used.

Survival

Mice were sacrificed when they reached at least one of the predefined criteria: i) lost of ≥15% of their maximal weight, ii ≥20 s to move back when placed on their back (maximum criteria on the paralysis evaluation scale). Kaplan-Meier survival curves were then compared using Graphpad prism v.6.

Mice overexpressing mutated SOD1 G93A were treated with Vehicle or compound (1) by oral administration every day from weaning (post-natal day 30) to final stage (complete paralysis of rear paws). Every week, muscle function was monitored using a grip test. Data indicate that treatment with compound (1) delayed the onset of the symptoms, which remained significantly improved as long as the muscle function was measured until 16 weeks of age (FIG. 6A). In addition, treatment with compound (1) significantly increased life span of mice compared to treatment with vehicle alone (FIG. 6B), thereby providing in vivo support for the neuroprotective effect of the compounds of the invention in a neurodegenerative mouse model.

Long-Term Memory Test-Inhibitory Avoidance (IA)

IA test is a well-established memory paradigm in rodents that measures contextual memory associated with a mild electrical footshock in a specific context (the dark compartment of the IA chamber). Groups of 8-week old C57Bl/6 wild-type female mice were tested. Each mouse was handled for 5 minutes per day for at least 4 consecutive days to reduce animal's stress due to experimenter's presence/manipulation during test days. Inhibitory avoidance was carried out in an IA chamber (MedAssociates) that consists in a rectangular Perspex box divided into a safe and a shock compartment separated by an automatically operated sliding door. The safe compartment is white and illuminated while the shock compartment is black and dark. Mice were trained for IA 20 min after oral administration of the drug or vehicle. During training, mice were placed into the safe compartment with their heads facing away from the door. After 10 seconds, the door separating the compartments was automatically opened, allowing the mouse to access the shock compartment (which it usually did within 20 sec). The door closed 1 second after the mouse entered the dark compartment, and a 2-second 0.6 mA intensity footshock was delivered to the grid floor of the shock chamber via a constant current scrambler circuit. After footshock delivery, mice stayed for 10 seconds in the dark compartment and were then returned to their home cages. Memory retention was measured at 24 h or 3 weeks after training by placing the mouse back into the lit compartment and recording its latency (in seconds) to enter the dark compartment. No footshock was administered during retention tests. The test was terminated once the mouse entered the dark compartment, or after a 900 seconds cutoff limit.

Statistical analyses were done using Graphpad prism v.6 using unpaired or paired 2-way Student's t-test for pairwise comparisons, or one-way ANOVA followed by Dunnett or Bonferroni post-hoc tests (Ludbrook, 1998, Clin Exp Pharmacol Physiol, 25(12):1032-7) when appropriate for multiple pair-wise comparisons.

Figure 7:
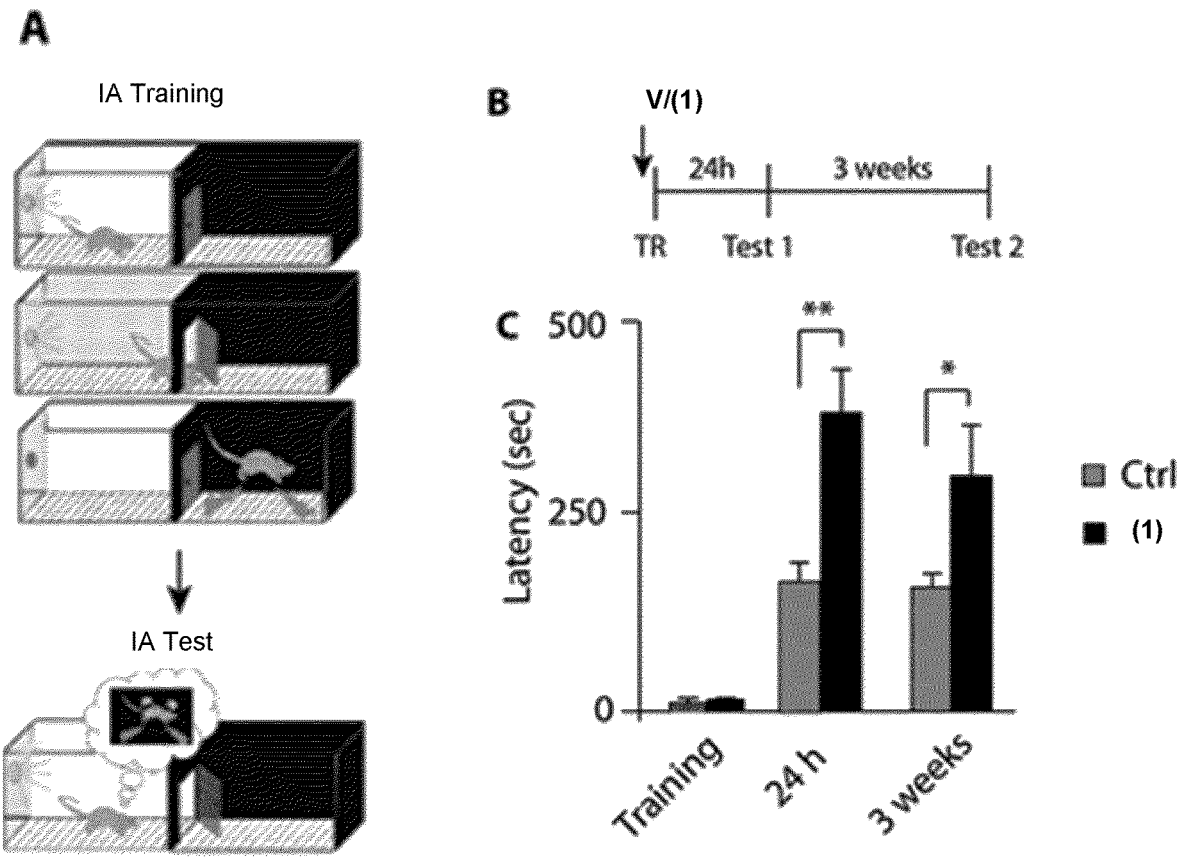
FIG. 7 shows the cognitive effect of compound of the invention (1) in the mouse model of inhibitory avoidance (IA) as described in Example 2. A: Schematic representation of the task, including training (mild electrical footshock received in the dark compartment of an IA apparatus) and testing (latency of the mouse to go back to the dark compartment of an IA apparatus); B: Experimental schedule; C: Latencies of mice treated before training with Vehicle (V) or compound (1) (100 mg/kg) to enter the dark compartment of an IA apparatus at training, at Test 1 (24 h after training) and at Test 2 (3 weeks after training). Data are shown as group average of latency values±SEM; n=8-9; *p<0.05, **p<0.01.

Memory was measured after oral administration of vehicle or compound (1) (100 mg/kg) to young adult male mice orally, and 20 min later a training for IA (FIG. 7). 24 hours and 3 weeks after training, latencies of mice to enter back into the dark compartment of the IA chamber, the place where they received the shock, were measured. Results indicate that all mice had same latencies at training (no motor or cognitive differences), while their latencies were significantly higher when treated with compound (1) compared to vehicle at both 24 h hours and 3 week-time points (FIG. 7C). These data indicate that treatment with a single dose of compound (1) (100 mg/kg) before training enhances long-term memory consolidation and/or expression.

Altogether, those data support that compounds of the invention stimulate lactate secretion, glucose uptake, and glycogenolysis by astrocytes in vitro. In addition, those data support that compounds of the invention enhance the above-described metabolic pathways in GLUT1 deficient astrocytes, which is an in vitro model of the GLUT1-DS.

Example 4: In Vivo Effects of Compounds of the Invention in Transgenic Mouse Model of GLUT1-DS.

To assess for the effect in vivo of the compounds of the invention, those were tested in the following model.

Transgenic mice on 129/SvJ genetic background in which GLUT1 has been knocked-down (GLUT1-DS mice) were used (Wang et al., 2016, *Human Molecular Genetics*, 15(7)). Mating colonies were composed of wild-type female mice and GLUT1-DS male mice, or GLUT1-DS female mice and wild-type male mice. F1 pups were genotyped after ear punching at weaning using PCR to determine genotype. Mice of 2 to 3 months of age were used.

Cerebral extracellular levels of lactate and glucose were monitored in vivo in GLUT1-DS transgenic male mice and wild-type (WT) male littermates using lactate and glucose biosensors (Pinnacle Technology), according to the manufacturer's instructions. GLUT1 DS transgenic mice and wild-type littermates, cannulae were surgically implanted in the left and right medial prefrontal cortices (coordinates: −1.0 mm (to bregma), lateral +/−1.0 mm (to mideline), ventral −1.0 mm (to dura)) 1). After surgery, mice were monitored closely and received analgesic treatment for at least 4 days. After mice had fully recovered from surgery, compounds of the invention of vehicle were administered per os as previously described and cerebral levels of extracellular lactate or glucose were dynamically recorded for 6 hours using lactate or glucose biosensors, respectively. Mice were administered orally vehicle alone first, followed 3 hours later by vehicle or Compound (1) at a dose of 10 or 100 mg/kg. During recording, mice were exposed to novel objects in their cages that consisted in plastic colored building blocks to stimulate their activity. Concentration of cerebral extracellular lactate or glucose was calculated from lactate or glucose probe electric signals, respectively, using post-calibration values, as described by manufacturer. Area Under the Curve (AUC) of lactate or glucose concentration curves were calculated using Graphpad Prism and the ratio of AUC after drug over Vehicle administration was calculated. AUC signals of lactate or glucose after vehicle or Compound (1) administration were expressed as fold change relative to AUC of lactate or glucose fluctuation following the first administration of vehicle (FIG. 7). Results indicate that treatment with Compound (1) at 10 mg/kg and/or 100 mg/kg significantly increases extracellular lactate or glucose levels in the brain of treated WT and GLUT1 DS transgenic mice, as compared to vehicle.

Figure 8:
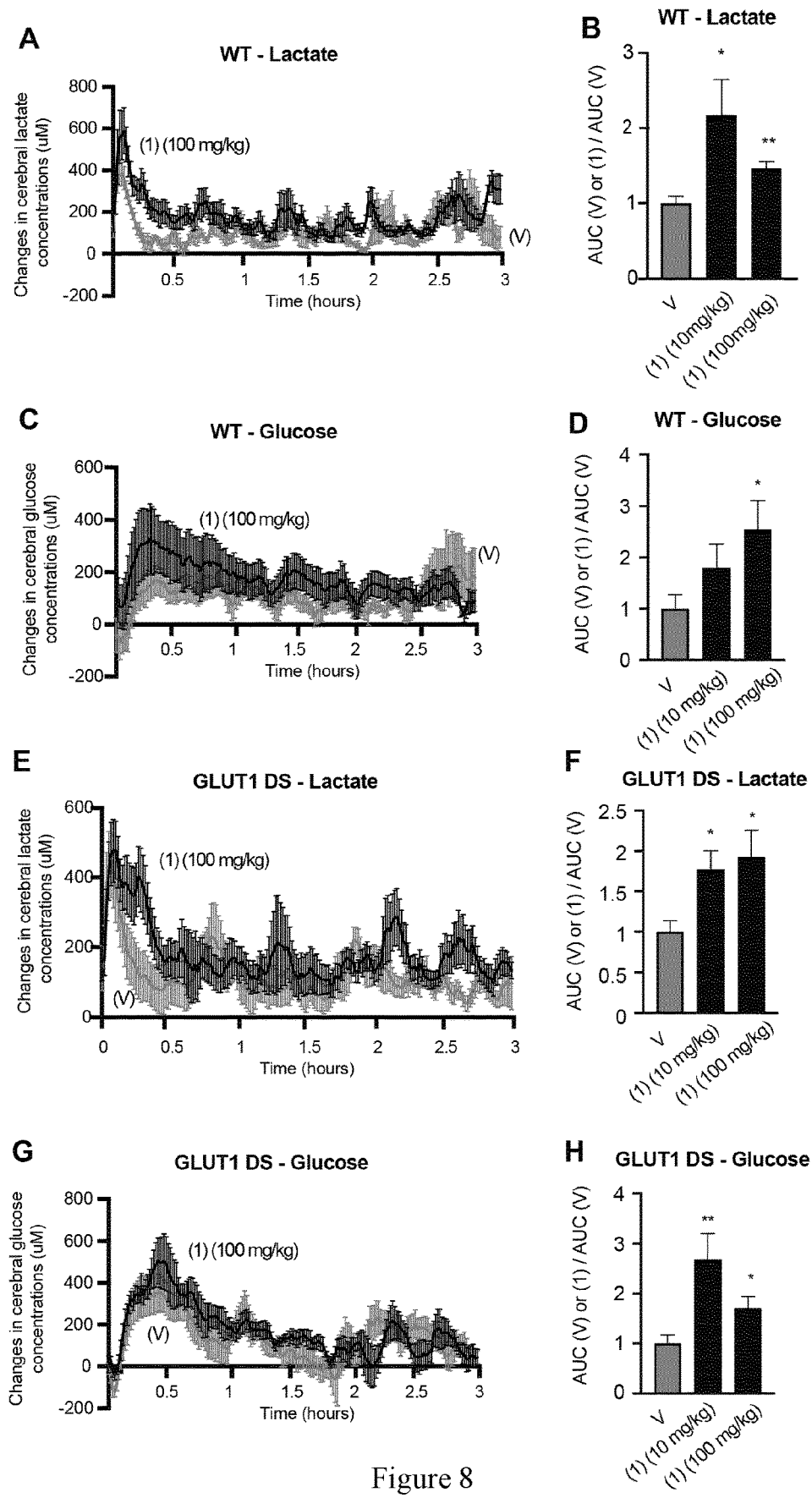
FIG. 8 shows the Extracellular lactate levels recorded in mice as described in Example 4. in (A-D) in the medial prefrontal cortex: wild-type (WT) mice (A) or GLUT1-DS mice (C) using L-lactate biosensors during 3 hours following oral administration of Veh (V) or Compound (1) at 100 mg/kg. Area under the curve (AUC) of lactate levels in (A) and (C) is shown as the ratio of AUC of Veh (V), Compound (1) at 10 mg/kg or Compound (1) at 100 mg/kg over AUC of Veh (V) in same mouse, in wild-type (WT) mice (B) or GLUT1-DS mice (D). (E-H) in the medial prefrontal cortex: wild-type mice (E) or GLUT1-DS mice (G) using glucose biosensors during 3 hours following oral administration of Veh (V) or Compound (1) at 100 mg/kg. Area under the curve (AUC) of glucose levels in (E) and (G) was calculated, and is shown as the ratio of AUC of Veh (V), Compound (1) at 10 mg/kg or Compound (1) at 100 mg/kg over AUC of Veh (V) in same mouse, in wild-type (WT) mice (F) or GLUT1-DS mice (H). Data are shown as the average±S.E.M of n=5-6 mice per group. Statistical analyses consisted in one-way ANOVA followed by Dunnett's post-hoc test, using Graphpad Prism v.9 (*, p<0.05; , p<0.01; *, p<0.001).
Figure 9:
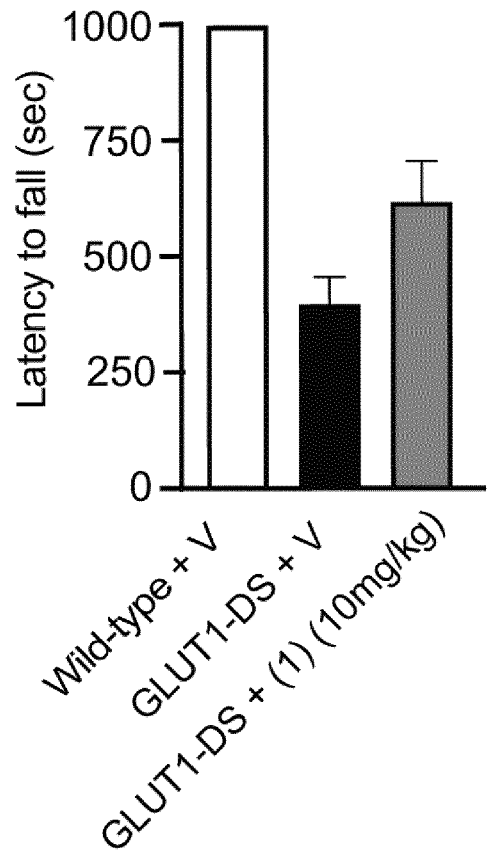
FIG. 9 represents the latency of mice (Wild-type (WT) and GLUT1-DS mice) before falling down the rotarod at a constant speed of 25 r.p.m. for a maximal duration of 1000 seconds or 1000 seconds for animals that did not fall down as described in Example 4. Data are shown as average +S.E.M of n=7-8 per group.

Motor function was measured in wild-type (WT) and GLUT1-DS transgenic mice in the rotarod after 19-day long treatment with Veh. or Compound (1). Mice were administered every day orally vehicle or Compound (1) at a dose of 10 mg/kg. After 14 days of treatment, mice were exposed to rotarod training, which consisted in placing the mouse on an accelerating rotarod (4 to 40 r.p.m.) during 300 seconds. Mice that felt down before training ended, or at the end of training (300 seconds), were removed and put back to their cages. Training took place over 4 consecutive days, and on each training day mice performed 3 consecutive trials with 15 min inter-trial duration. One day after the last training (on the fifth day), mice were tested on the rotarod. Testing consisted in placing mice on the rotarod at a constant speed of 25 r.p.m. Latencies of mice before falling down were recorded. Mice that did not fall for a maximal duration of 1000 seconds were removed and test was terminated. These data are presented on FIG. 8 and indicate that GLUT1-DS transgenic mice had poor performance on the rotarod compared to WT mice, while administration of Compound (1) at a dose of 10 mg/kg for 19 days increased rotarod performance in GLUT1 mice.

ing administering in a subject in need thereof a therapeutically effective amount of a compound of Formula (I)

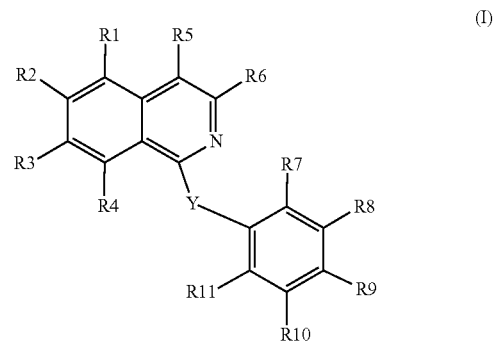

wherein $R^1$, $R^2$, $R^3$, $R^4$, $R^5$ and $R^6$ are independently selected from H, halogen, optionally substituted alkoxy, optionally substituted $C_1$-$C_6$ alkyl, optionally substituted amine, optionally substituted carboxylic acid or ester, nitro and nitrile; $R^7$, $R^8$, $R^9$, $R^{10}$ and $R^{11}$ independently selected from H, halogen, optionally substituted alkoxy, optionally substituted $C_1$-$C_6$ alkyl, optionally substituted amine, optionally substituted carboxylic acid or ester, nitro and nitrile and a group of Formula (II): —$(X)_m$—$CR^{12}R^{13}R^{14}$ (II) wherein at least one group of $R^7$, $R^8$, $R^9$, $R^{10}$ and $R^{11}$ is a group of Formula (II); X is selected from O, $NR^{15}$, S, $SO_2$, $CH_2$ and hydrazine (—N—N—), m is an integer elected from 0 and 1 and $R^{12}$, $R^{13}$ and $R^{14}$ are independently selected from H, OH, optionally substituted alkoxy, amide, pyrrolidone, nitrile, optionally substituted $C_1$-$C_6$ alkyl and halogen; Y is selected from —$CR^{16}R^{17}$— and —$NR^{18}$—; $R^{15}$ is selected from H, optionally substituted alkoxy and optionally substituted $C_1$-$C_6$ alkyl; $R^{16}$ and $R^{17}$ are independently selected from H, halogen, optionally substituted alkoxy, optionally substituted $C_1$-$C_6$ alkyl and optionally substituted aryl; R18 is independently selected from H or option-

The invention claimed is:

1. A method of treating Glucose transporter 1 deficiency syndrome (GLUT1-DS) in a subject, said method comprisally substituted C1-C6 alkyl; pharmaceutically acceptable salts, hydrates, solvates or mixtures thereof.

2. The method according to claim 1, wherein at least one of $R^{12}$, $R^{13}$ and $R^{14}$ is F or Cl.

3. The method according to claim 1, wherein X is selected from O, $NR^{15}$, S, $SO_2$, and hydrazine (—N—N—).

4. The method according to claim 1, wherein Y is —$NR^{18}$.

5. The method according to claim 1, wherein Y is —$CR^{16}R^{17}$.

6. The method according to claim 1, wherein $R^1$, $R^4$, $R^5$ and $R^6$ are H.

7. The method according to claim 1, wherein $R^1$ is H or optionally substituted $C_1$-$C_6$ alkyl.

8. The method according to claim 1, wherein $R^1$ is optionally substituted amine.

9. The method according to claim 1, wherein $R^2$ and $R^3$ are selected from H, methoxy and optionally substituted alkoxy.

10. The method according to claim 1, wherein $R^8$ is H.

11. The method according to claim 1, wherein $R^8$ is optionally a substituted alkoxy, $OCF_3$ or $OCHF_2$.

12. The method according to claim 1, wherein $R^8$ is halogen.

13. The method according to claim 1, wherein $R^9$ is a group —$(X)_m$—$CR^{12}R^{13}R^{14}$.

14. The method according to claim 1, wherein m is 1.

15. The method according to claim 1, wherein X is O.

16. The method according to claim 1, wherein X is S.

17. The method according to claim 1, wherein $R^{12}$, $R^{13}$ and $R^{14}$ are F.

18. The method according to claim 1, wherein $R^{10}$ and $R^{11}$ are H.

19. The method according to claim 1, wherein $R^7$, $R^8$, $R^{10}$ and $R^{11}$ are H.

20. The method according to claim 1, wherein $R^9$ is $OCF_3$ or $OCF_3$.

21. The method according to claim 1, wherein $R^9$ is H.

22. The method according to claim 1, wherein said compound is selected from the group consisting of:
- 6,7-dimethoxy-N-(4-(trifluoromethoxy)phenyl)isoquinolin-1-amine;
- 6,7-dimethoxy-N-(4-(trifluoromethyl)phenyl)isoquinolin-1-amine;
- N-(4-(trifluoromethoxy)phenyl)isoquinolin-1-amine;
- 6,7-dimethoxy-1-(4-(trifluoromethoxy)benzyl)isoquinoline;
- N-(3,4-dimethoxyphenyl)-6,7-dimethoxyisoquinolin-1-amine;
- 6,7-dimethoxy-N-(p-tolyl)isoquinolin-1-amine;
- 6,7-dimethoxy-N-(4-methoxyphenyl)isoquinolin-1-amine;
- 6,7-dimethoxy-N-(4-(2-methoxyethoxy)phenyl)isoquinolin-1-amine;
- 6,7-dimethoxy-N-(4-(methoxymethyl)phenyl)isoquinolin-1-amine;
- N-(2-fluoro-4-(trifluoromethoxy)phenyl)-6,7-dimethoxyisoquinolin-1-amine;
- 6,7-dimethoxy-N-(3-(trifluoromethoxy)phenyl)isoquinolin-1-amine;
- 6-methoxy-N-(4-(trifluoromethoxy)phenyl)isoquinolin-1-amine;
- 6-chloro-N-(4-(trifluoromethoxy)phenyl)isoquinolin-1-amine;
- N-(3-fluoro-4-(trifluoromethoxy)phenyl)-6,7-dimethoxyisoquinolin-1-amine;
- $N^1$-(6,7-dimethoxyisoquinolin-1-yl)-$N^3$,$N^3$-dimethylbenzene-1,3-diamine;
- N-(3-(difluoromethoxy)phenyl)-6,7-dimethoxyisoquinolin-1-amine;
- 4-((6,7-dimethoxyisoquinolin-1-yl)amino)-3-(trifluoromethyl)benzo-nitrile;
- 6,7-dimethoxy-N-(4-(methylthio)phenyl)isoquinolin-1-amine;
- N-(3-chloro-4-(trifluoromethoxy)phenyl)-6,7-dimethoxyisoquinolin-1-amine;
- 6,7-dimethoxy-N-(4-(2-methoxyethyl)phenyl)isoquinolin-1-amine;
- 6-methoxy-5-methyl-N-(4-(trifluoromethoxy)phenyl)isoquinolin-1-amine;
- 6-methoxy-$N^5$,$N^5$-dimethyl-$N^1$-(4-(trifluoromethoxy)phenyl)isoquino-line-1,5-diamine;
- 4-chloro-6-methoxy-N-(4-(trifluoromethoxy)phenyl)isoquinolin-1-amine;
- 6-methoxy-4-methyl-N-(4-(trifluoromethoxy)phenyl)isoquinolin-1-amine;
- 4-bromo-6-methoxy-N-(4-(trifluoromethoxy)phenyl)isoquinolin-1-amine;
- 6-methoxy-4-methyl-N-(4-(trifluoromethoxy)phenyl)isoquinolin-1-amine;
- $N^6$,$N^6$-dimethyl-$N^1$-(4-(trifluoromethoxy)phenyl)isoquinoline-1,6-diamine;
- 1-((4-(trifluoromethoxy)phenyl)amino)isoquinoline-6-carbonitrile;
- methyl 1-((4-(trifluoromethoxy)phenyl)amino)isoquinoline-6-carboxylate; and
- 6-ethyl-N-(4-(trifluoromethoxy)phenyl)isoquinolin-1-amine; and
- any pharmaceutically acceptable salts, hydrates, solvates and mixtures thereof.

23. The method according to claim 1, wherein the administration of a therapeutically effective amount of the compound of Formula (I) treats and/or stabilizes GLUT1-DS.

24. The method according to claim 1, wherein the treatment increases cognitive performance, reduces epileptic seizures, improves motor function or reduces the severity of movement disorders in the subject.

* * * * *

SEQUENCE LISTING

<160> NUMBER OF SEQ ID NOS: 2

<210> SEQ ID NO 1
<211> LENGTH: 19
<212> TYPE: RNA
<213> ORGANISM: Artificial sequence
<220> FEATURE:
<223> OTHER INFORMATION: Scramble siRNA

<400> SEQUENCE: 1
agguagugua aucgccuug                                        19

<210> SEQ ID NO 2
<211> LENGTH: 19
<212> TYPE: RNA
<213> ORGANISM: Artificial sequence
<220> FEATURE:
<223> OTHER INFORMATION: GLUT1 siRNA

<400> SEQUENCE: 2
guauagaugg aagauauuu                                        19